United States Patent [19]

Durham et al.

[11] Patent Number: 5,070,246
[45] Date of Patent: Dec. 3, 1991

[54] SPECTROMETER FOR MEASURING THE CONCENTRATION OF COMPONENTS IN A FLUID STREAM AND METHOD FOR USING SAME

[75] Inventors: Michael D. Durham, Castle Rock; Donald H. Stedman, Englewood; Timothy G. Ebner, Westminster; Mark R. Burkhardt, Englewood, all of Colo.

[73] Assignee: ADA Technologies, Inc., Englewood, Colo.

[21] Appl. No.: 410,925

[22] Filed: Sep. 22, 1989

[51] Int. Cl.$^5$ .............................................. G01J 3/32
[52] U.S. Cl. .................................... 250/373; 250/341; 356/436
[58] Field of Search ............... 250/373, 340, 341, 343; 356/51, 436

[56] References Cited

U.S. PATENT DOCUMENTS

| | | | |
|---|---|---|---|
| 2,170,435 | 8/1939 | Sweeney | 73/51 |
| 2,620,444 | 12/1952 | Heigl et al. | 250/43.5 |
| 2,690,093 | 9/1954 | Daly | 88/14 |
| 3,637,310 | 1/1972 | Naono | 356/83 |
| 3,640,625 | 2/1972 | Ibbett et al. | 356/97 |
| 3,702,736 | 11/1972 | Coggeshall | 356/96 |
| 3,732,017 | 5/1973 | Wolber | 356/201 |
| 3,880,523 | 4/1975 | Thomas | 356/79 |
| 3,893,770 | 7/1975 | Takami et al. | 356/96 |
| 3,929,398 | 12/1975 | Bates | 356/186 |
| 3,973,849 | 8/1976 | Jackson et al. | 356/97 |
| 4,054,389 | 10/1977 | Owen | 356/189 |
| 4,158,505 | 6/1979 | Mathisen et al. | 356/308 |
| 4,563,585 | 1/1986 | Ward | 250/373 |
| 4,566,792 | 1/1986 | Suzuki | 356/319 |
| 4,571,074 | 2/1986 | Thevenon | 356/51 |
| 4,678,917 | 7/1987 | Helms et al. | 250/373 |
| 4,746,793 | 5/1988 | Hopkins, II | 250/237 |
| 4,914,719 | 4/1990 | Conlon et al. | 250/343 |

OTHER PUBLICATIONS

"Development of Low Level NH$_3$ Measuring Method," Nakabayashi et al.
"Photodiode Array Detectors for LC," by Stuart A. Borman, Analytical Chemistry, 55 (8) Jul. 1983, pp. 836A-842A.
"Continuous Infrared Analysis of N$_2$O in Combustion Products," by T. A. Montgomery and G. S. Samuelson, JAPCA, vol. 39, No. 5, May 1989, pp. 721-726.

Primary Examiner—Jack I. Berman
Assistant Examiner—Richard Hanig
Attorney, Agent, or Firm—Sheridan, Ross & McIntosh

[57] ABSTRACT

A device and method for measuring the concentrations of components of a fluid stream. Preferably, the fluid stream is an in situ gas stream, such as a fossil fuel fired flue gas in a smoke stack. The measurements are determined from the intensity of radiation over a selected range of radiation wavelengths using peak-to-trough calculations. The need for a reference intensity is eliminated.

42 Claims, 14 Drawing Sheets $NH_3$ calibration curve generated using the linear regression algorithm.

SPECTROMETER FOR MEASURING THE CONCENTRATION OF COMPONENTS IN A FLUID STREAM AND METHOD FOR USING SAME

This invention was made with Government support under Contract No. DE-AC02-88ER80612 awarded by the Department of Energy. The Government has certain rights in this invention.

FIELD OF THE INVENTION

The present invention is directed to the field of spectrometry, and in particular spectrometers employing photodiode arrays for measuring the concentration of components in a fluid stream.

BACKGROUND OF THE INVENTION

Spectrometers have been used to determine the concentration of fluids and the concentration of components found in mixtures of fluids. For example, the absorption characteristics of a gas at specific radiation wavelengths can be used to identify and quantify the concentration of the gas. This process is best defined by the Beer-Lambert law, which states that the transmittance of radiation through a gas that absorbs radiation is decreased exponentially and directly proportional to the length of the radiation path and the concentration of the gas. This relationship is shown in Equation 1:

$$T = I/I_o = e^{-acl} \quad (1)$$

where:
T = transmittance of the radiation through the gas
$I_o$ = intensity of the radiation entering the gas
I = intensity of the radiation leaving the gas
a = molar absorptivity
c = concentration of the gas
l = distance the radiation beam travels through the gas The molar absorptivity, a, is dependent upon the wavelength of the radiation and upon the characteristics of the gas. The molar absorptivity indicates the degree to which a molecule will absorb radiation at a given wavelength. This can be determined by calibration on a given spectrometer. The molar absorptivity is a constant. Thus, once it is determined for a given spectrometer, it should theoretically not have to be determined again for that spectrometer.

In most spectrometers, it is not practical to measure the radiation intensities I and $I_o$ simultaneously. Therefore, the initial intensity, $I_o$, is determined by a measurement made during a calibration step in which all radiation absorbing gases are purged from the sample cell. However, purging is costly, both in terms of added equipment cost and added labor costs. Additionally, purging is often impractical when a sample cell is not employed, i.e. during in situ measurements. The transmittance of the zero gas is by definition 100%. The spectrum obtained is the reference spectrum with which subsequent spectra are compared to determine the transmittance.

In an alternative method, the radiation beam path can be alternated between a reference path and the sample path, as disclosed in U.S. Pat. No. 4,158,505 by Mathisen et al. issued June 19, 1979. However, as can be seen from this patent, complicated mechanisms are required in order to provide for the switching of the beam between the reference and sample paths. Additionally, errors can be introduced if the reference and sample paths are not identical.

If more than one gas absorbs at the wavelength of interest, Beer's law dictates that the absorbance of a mixture is the sum of the absorbances of all the components of the mixture U.S. Pat. No. 3,893,770 by Takami et al. issued July 8, 1975, describes an apparatus for analyzing a plurality of mixed gases. The disclosed analyzer can measure component gases e.g. nitrogen dioxide ($NO_2$), sulfur dioxide ($SO_2$) and nitric oxide (NO), present in flue gases. It relies on detection of absorption spectra by simultaneous measurement of the intensity of radiation at several different discrete wavelengths. Interferences between spectra of different gases are compensated for by means of appropriate function generation and arithmetic units in the system's output circuitry. The interferences must be "irreversible" in order for the unit to operate. Additionally, a means must still be provided in order to obtain the initial reference intensity, $I_o$, in order to calculate the relative absorbances.

Another difficulty encountered in using an instrument of the type disclosed in U.S. Pat. No. 3,893,770 for characterizing components in flue gas is due to the environment in which the instrument has to operate. Since the instrument is measuring only a single wavelength of the spectrum for each gaseous component, any misalignment due to vibration or temperature or pressure gradients will produce inaccuracies in the measurement. In addition, the accuracy of the absorbance calculation is dependent upon the stability of the reference measurement. Since the reference measurement cannot be made continuously, any change in the output of the radiation source or distortion in the optics will produce a source of error.

In an article entitled "Development of Low Level $NH_3$ Measuring Method" by Nakabayashi et al., a method for measuring $NH_3$ at low concentrations is disclosed. In this method, the need for obtaining a reference intensity level, $I_o$, is eliminated. However, wavelength modulation of a certain angular frequency must be applied at a wavelength corresponding to an absorption peak. This requires the use of an oscillating mirror or slit. Such a moving mechanism in a spectrometer could be a source of error if the oscillation frequency were to deviate or the orientation of the mirror or slit were to become misaligned.

Another problem with the Nakabayashi device is that it requires frequent calibration. For example, a method for dealing with interference from $SO_2$ is disclosed, however, weekly calibration of the instrument is required. In addition, a zero point calibration must be carried out every six hours. Such frequent calibrations are obviously undesirable.

The Nakabayashi device is also very sensitive to temperature shifts and, therefore, must be housed in a constant temperature chamber and heated to a temperature of 43° C. Additionally, the sample path must be heated to a temperature of 300° C. in order to avoid the deposition of acid ammonium sulfate, which occurs below 250° C.

Therefore, it would be advantageous to have a spectrometer which does not require frequent mechanical calibrations.

It would also be advantageous to have a spectrometer which can be used to measure the concentration of gases in the presence of other interfering gases.

Further, it would be advantageous to be able to measure the concentration of gases continuously.

Additionally, it would be advantageous to measure the concentration of gases without having to periodically obtain a reference, or zero gas, measurement.

Furthermore, it would be advantageous to have a spectrometer with few moving parts.

Also, it would be advantageous to have a spectrometer which could be used both in situ and in an extractive environment.

Further, it would be advantageous to have a spectrometer in which variations in the intensity of the radiation source did not affect the accuracy of measurements.

SUMMARY OF THE INVENTION

In accordance with the present invention, a method and apparatus for measuring the concentration of components in a fluid stream is provided.

In a preferred method, the measurement of in situ fluid streams is provided. The method includes the steps of passing a radiation beam through the in situ fluid stream, selecting a range of wavelengths in which the desired component absorbs radiation, measuring the amount of radiation which passes through the fluid stream at a plurality of different wavelengths within the selected range and calculating the concentration of the desired component by determining the difference in amount of radiation which passes through the stream at at least two different points within the selected range.

Preferably, the method for calculating the concentration of the desired component includes the steps of determining a first wavelength at which a minimal amount of transmitted radiation occurs within the selected range, calculating a base line by performing a linear regression calculation on two groups of transmitted radiation values corresponding to wavelengths both above and below the first selected wavelength, determining the difference between the minimal transmitted radiation value and the transmitted radiation value on the base line at the first wavelength and calculating the concentration of the component based on calibration curves obtained from previous measurements performed on fluids containing components of known concentrations.

A preferred apparatus for performing the process of the present invention includes a radiation source, a radiation detection means for measuring transmitted radiation through a fluid stream at a plurality of wavelengths within a selected wavelength range, optics for directing radiation from the radiation source through the fluid stream and onto the radiation detection means, and a device for calculating the concentration of a component in the fluid stream, by employing the transmitted radiation values obtained for the selected wavelength range and reference values obtained by measuring relative transmitted radiation for gases of known concentration within the selected wavelength range.

DETAILED DESCRIPTION OF THE INVENTION

The device of the present invention is designed to measure the concentration of components in a fluid stream. Preferably, the present device measures the concentration of gaseous components in a gas stream.

A preferred embodiment of the device provides a quantitative measurement of ammonia ($NH_3$) in a flue gas stream in the presence of interfering gases such as sulfur dioxide ($SO_2$) and nitric oxide (NO).

Figure 1:
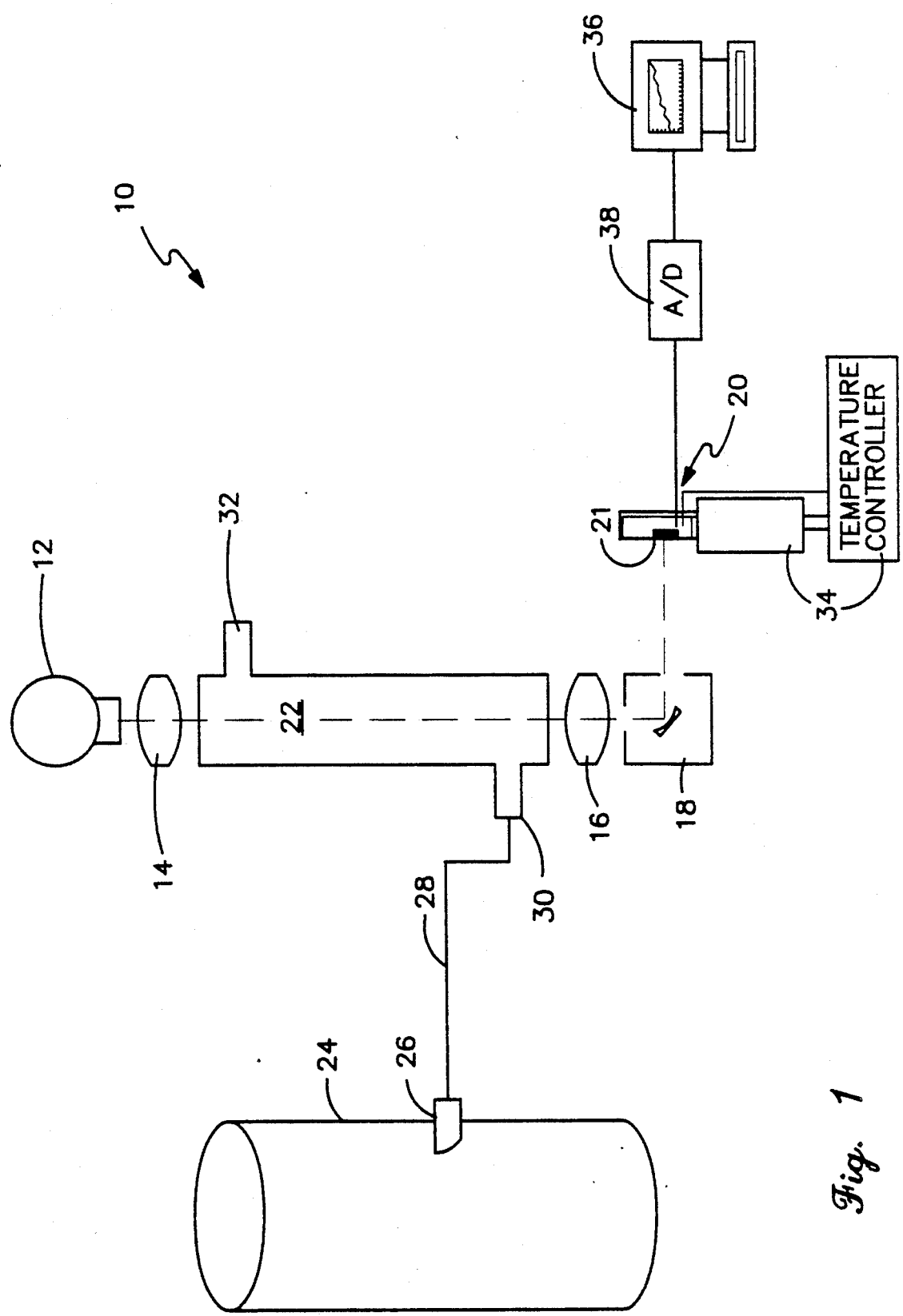
FIG. 1 illustrates a preferred embodiment of an extractive spectrometer in accordance with the present invention.

A preferred embodiment of the present apparatus is illustrated in FIG. 1. The instrument 10 includes a radiation source 12. Preferably, the radiation source 12 is a source of ultraviolet and visible radiation in the wavelength region of 1900 to 6000 Angstroms. The radiation source 12 is energized by a power supply (not shown) designed to provide a constant current. Sufficient optics, including lenses 14 and 16, as well as mirrors and windows (not shown) are provided to focus the radiation beam from the radiation source 12 at the entrance to a polychromator 18. Preferably, the polychromator 18 comprises a prism or an optical grating as well as internal means whereby the radiation is collimated and focused, as appropriate. The polychromator 18 disperses the radiation from the radiation source 12 across a radiation detector 20. Preferably, the radiation detector 20 comprises a linear photodiode array 21. The polychromator 18 can be physically adjusted to provide analysis of more than one wavelength region of interest. The wavelength resolution of the instrument 10 is defined by the optics, particularly optics within the polychromator 18 and the detector 20, and the geometric spacing between the polychromator 18 and the radiation detector 20.

The radiation detector 20 preferably includes a linear photodiode array 21, which is placed across the focal plane of the polychromator 18. A linear photodiode array is a large scale, integrated circuit fabricated on a single monolithic silicon crystal. It consists of an array of diodes, or pixels, each acting as a radiation-to-charge transducer and a storage device. Linear photodiode arrays are well suited for use in ultraviolet spectrometers because they have a large quantum efficiency, e.g. 40% to 80%, throughout the ultraviolet range as well as geometric, radiometric, and electronic stability. Linear photodiode arrays are very tolerant of humidity, vibration and electromagnetic fields.

The linear photodiode array 21 is located in the focal plane of the polychromator 18 so that each diode corresponds to a particular wavelength resolution of the spectrum produced by the polychromator 18. The linear photodiode array 21 provides an efficient sensor for the digital acquisition of spectra, because the array 21 itself, by its presence in the focal plane of the polychromator 18, digitizes the spectrum into discrete intervals corresponding to wavelengths. Unlike scanning spectrometers of the prior art, whose wavelength accuracy is mechanically limited, the linear photodiode array spectrometer is limited only by geometric constraints of the detector itself, by vibration and thermal expansion of the optical components, and by the stability of the radiation source 12. Wavelength accuracy is equivalent to diode spacing multiplied by the linear dispersion of the polychromator. The geometric registration and, therefore, its wavelength accuracy and precision, are typically better than mechanically scanned spectrometers. The linear photodiode array 21 is also advantageous in that it provides an instantaneous spectrum which can be used for determining the gas concentration of different gases. Preferably there are from about 500 to about 1000 individual linear photodiodes in the array, with a center-to-center distance of about 25 micrometers between each diode.

The resolution of the photodiode array plays an important role in the accuracy of the instrument. Therefore, the appropriate resolution for any given instrument will be determined in part by the desired accuracy. For present purposes, the resolution will be expressed in terms of "wavelength (measured in Angstroms) per diode." It has been found that if the resolution is too low (i.e., the wavelength per diode value is too high) interference between adjacent peaks of a spectrum may result. However, if the resolution is too high (i.e., the wavelength per diode value is too low), then the range of wavelengths which fall upon the entire photodiode array will be too small to be useful. It has been found that for the measurement of gases such as $NH_3$, $SO_2$ and $NO$, a resolution between about one Angstrom per diode and four Angstroms per diode works satisfactorily. A resolution of one Angstrom per diode is preferred for measuring the concentration of these three gases. The affect of resolution will be discussed in more detail in connection with Example 6.

The fluid stream to be analyzed must flow between the radiation detector 20 and the radiation source 12. The polychromator 18 can be placed either before, after or within the fluid stream. The device 10 of the present invention is advantageous in that it can be used in either an extractive or an in situ system. The extractive approach, as illustrated in FIG. 1, involves the use of a gas cell 22 with windows at each end. Preferably the windows are made of a material which is highly transparent to ultraviolet radiation, e.g., fused silica or quartz glass. A sample of fluid, e.g. flue gas from a stack 24 (not to scale), is extracted by means of a probe 26 and transported to the gas cell 22 through a sample line 28. The gas sample then flows through the inlet 30 of the gas cell 22 where it is analyzed. The sample probe 26, sample line 28 and gas cell 22 can be heated to an appropriate temperature to prevent condensation and reactions between various components from occurring. The gas sample exits from the gas cell 22 via outlet 32.

Figure 2:
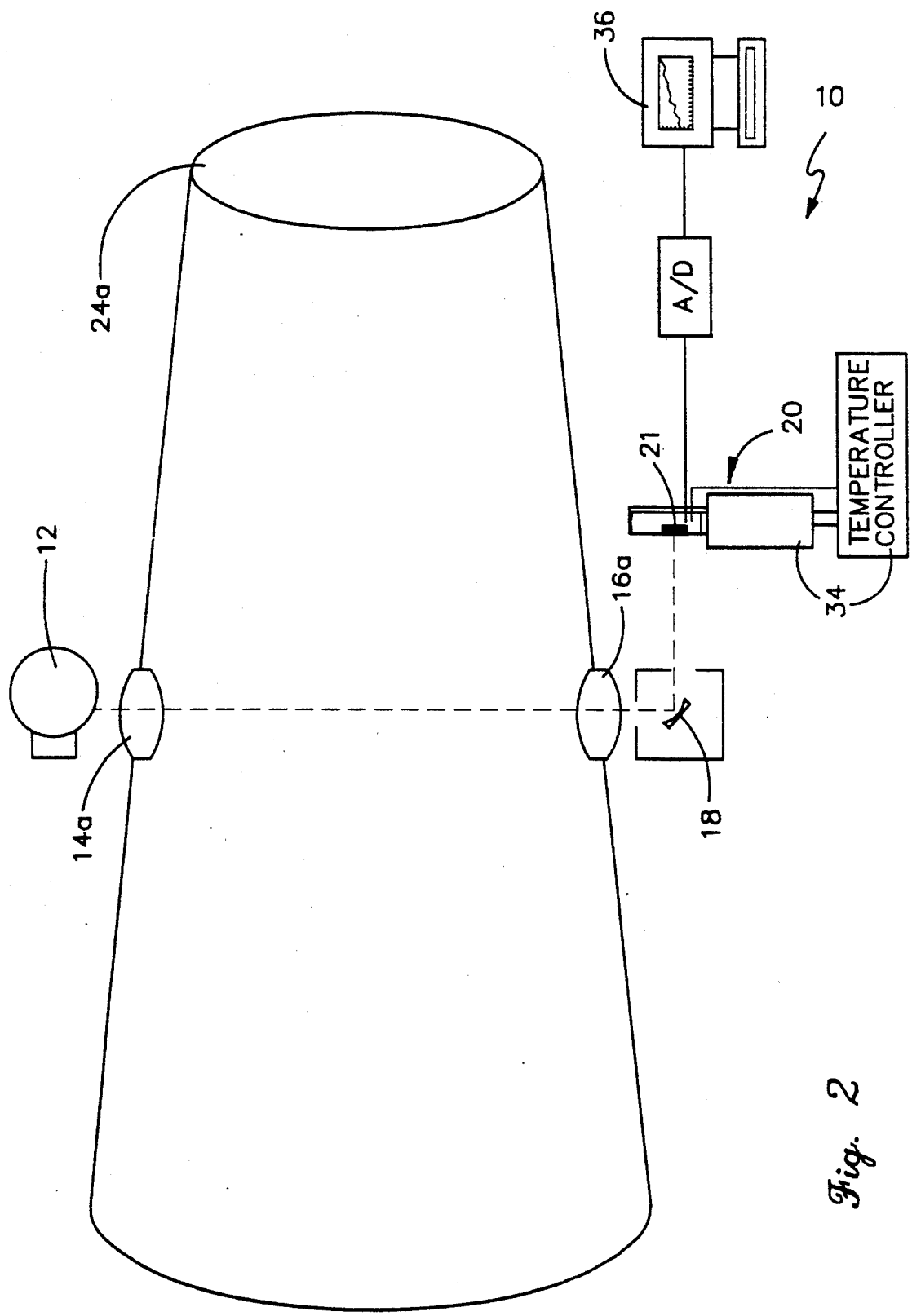
FIG. 2 illustrates a preferred embodiment of an in situ spectrometer in accordance with the present invention.

With an in situ system, as illustrated in FIG. 2, the radiation source 12, the polychromator 18 and the appropriate optics 14a and 16a are positioned such that the fluid flows between the radiation source 12 and the radiation detector 20 in its normal environment. For example, as illustrated in FIG. 2, a flue gas in a stack 24a flows between the radiation source 12 and the radiation detector 20 In a preferred embodiment, the radiation beam is reflected within the stack in order to obtain the desired pathlength In this manner, the source 12 and detector 20 can be located on the same side of the stack. The instrument 10a continuously analyzes the gas as it flows across the radiation beam. This arrangement is advantageous in that it eliminates the need for a sampling system, and its attendant heating devices, and it reduces the likelihood of artifacts forming during the sampling process Artifacts are prone to form in the gas cell 22 and sample line 28 (see FIG. 1) of an extractive device 10, especially if there is a temperature difference between the gas being analyzed and the gas cell 22 or sample line 28.

In a preferred embodiment, a temperature controlled cooler 34 is connected to the radiation detector 20 to provide a means to maintain a constant temperature for the detector 20, independent of fluctuations in the ambient conditions Linear photodiode arrays are manufactured from a silicon based substrate and their performance is affected by changes in operating temperature. Thermally-generated dark current represents a source of noise for linear photodiode array systems. The net effect of the dark current for uncooled or insufficiently cooled arrays is high noise in low-radiation-level situations or when strongly absorbing samples are present Dark current at long integration times, or for uncooled arrays, can rapidly reduce the maximum measurable signal.

A microprocessor 36 is employed to process the signals from the detector 20 to determine the concentration of component gases. Various algorithms, as described in more detail hereinbelow, are used to measure the intensity of transmitted radiation, account for changes in the intensity of the radiation, account for interferences, and check alignment. These algorithms reduce or eliminate the need for periodic mechanical calibrations.

In a preferred embodiment, each photodiode of the linear photodiode array 21 is connected to the output line of a field effect transistor (FET) switch, which is controlled by a single bit that is shifted through a shift register. When the FET switch is addressed, the diode is charged up to its full reverse-bias potential. The charging of each diode takes less than a microsecond; the multiplexer switching between elements occurs at a rate of 250 to 2000 kHz, depending upon the limitations of the analog/digital converter 38. The readout from the detector 20 is accomplished through the use of two transistor-transistor logic (TTL) level signals, a start pulse signal and a clock signal.

The analog signal from the common output line of the detector 20 is run through an amplifier sample-and-hold system to reduce noise. It is then digitized and transmitted to a microprocessor 36. The data can then be read out in real-time. This maximizes the amount of data. Various techniques, such as variable integration, diode grouping, or diode skipping, optimize the data collection relative to the analog/digital range, signal to noise ratio, and available digital memory, respectively.

With the present device 10 it is not necessary to compare the signal to a reference measurement (intensity value for zero gas, $I_o$, taken at another period of time) to determine the gas concentration. From Equation 1 it can be seen that the concentration is linearly related to log I. With the present spectrometer it is possible to use the log of the intensity, I, at two points within a wavelength range to determine the concentration. Although the relationships will be described in terms of log values, one skilled in the art will appreciate that ln values can also be used.

The difference between two selected points is measured for a specific gas at several known concentrations and used for calibration. An analysis program scans a given spectrum and determines the change in log intensity between a minimum (peak) and a maximum (trough) within a selected wavelength range. The minimum intensity is referred to as a "peak," because a low intensity is indicative of a high, or peak, absorbance.

The change in log intensity or "peak-to-trough height" is then plotted against the known concentration to form a calibration curve. A similar procedure is followed for an unknown concentration of the gas. The peak-to-trough height for the unknown concentration is compared to the calibration curve in order to determine the concentration. Naturally, this process can be programmed to be performed by a computer, using algorithms rather than actual plotted curves. This approach eliminates the need for an initial reference intensity, $I_o$, and simplifies and speeds the calculation of concentration. Since the analysis procedure searches for characteristic features of the absorption spectrum (i.e. peak and trough) rather than transmittance at some preselected, fixed wavelength, equipment deviations, such as drift and lamp intensity fluctuations are compensated for automatically.

The peak-to-trough height can be determined by first finding the minimum transmitted radiation value at a first wavelength within a preselected wavelength range, then measuring the difference between this minimum value and either a maximum transmitted radiation value within the range or a transmitted radiation value at a second wavelength which differs from the first wavelength by a set amount. This method will be described in more detail in Example 1. Alternatively, the peak-to-trough height can be calculated by first generating a base line and then measuring the difference between the minimum transmitted radiation value (i.e. the peak) and this base line at the wavelength of the peak.

In this second, or "baseline" method, the minimum transmitted radiation value is first determined within the selected wavelength range. Examples of preferred selected wavelength ranges for specific gases are: between about 2040 Angstroms and about 2120 Angstroms for $NH_3$, between about 2100 Angstroms and about 2200 Angstroms for NO and between about 2270 Angstroms and about 2300 Angstroms for $SO_2$. In an alternative embodiment, the preferred selected wavelength ranges for specific gases are: between about 2040 Angstroms and about 2120 Angstroms for $NH_3$, between about 2200 Angstroms and about 2300 Angstroms for NO, and between about 2170 Angstroms and about 2200 Angstroms for $SO_2$. Appropriate algorithms can be employed to automatically determine the minimum transmitted radiation in the selected range of wavelengths. After the minimum transmitted radiation is determined, two groups of transmitted radiation values are selected at wavelengths above and below the wavelength of the minimum transmitted radiation. A linear regression operation is performed on the two groups of points in order to produce the base line. The log value of the distance between the minimum transmitted radiation value and the base line is then determined. This log value is employed to calculate the concentration. This method will be explained in more detail in Example 5.

It should be appreciated that a reference value, $I_o$, does not have to be obtained in order to calculate the concentration in the manner provided by the present invention. This is an important advantage. All that is necessary is the appropriate peak-to-trough height and a predetermined calibration curve.

Another important advantage is that the present analysis program determines the minimum transmitted radiation within the selected wavelength range. Therefore, if for some reason the spectrum shifts relative to the photodiode array, the device is selfcorrecting. In other words, once the minimum is found, the software assigns this value the designation of the "peak value." The trough values are then selected relative to the peak value. The second derivative is used to locate the peak. The peak value can be thought of as being a "characteristic feature," around which the rest of the calculations are based. Because the program is designed to search out the peak value within a range, if the spectrum on the photodiode array shifts to the left or right, but remains in this range, the program is capable of automatically correcting for the shift without requiring mechanical calibrations.

It should be noted that although transmission values are discussed in terms of their respective wavelengths, in fact the computer program will typically correlate the transmitted radiation values to a photodiode array number rather than an actual wavelength. It makes no difference if the analysis program is searching for the characteristic feature, i.e. the peak, within a given range of wavelengths or within a given range of photodiode numbers. Any units can be employed, as long as they define a range.

In summary, the information required by the analysis program in order to calculate concentrations include: (1) a calibration curve or an equation defining a calibration curve, (2) a selected range, e.g. wavelength range, in which to search for a minimum transmitted radiation value (i.e. the "peak" value), and (3) instructions regarding how to determine the trough transmitted radiation value. As explained hereinbefore, the trough transmitted radiation value can be determined by merely finding the transmitted radiation value at a given distance away from the minimum transmitted radiation value. Alternatively, the trough can be determined by finding the maximum value in the selected wavelength range. In yet another alternative, a base line can be generated and the difference between the minimum value and the base line at a given wavelength can be determined.

As already pointed out, in the present method it is useful to know the minimum transmitted radiation value (peak value) within a selected range, and at least one local maximum value (trough value) at wavelengths above and/or below the wavelength of the minimum value. The maximum and minimum values can be determined by any method available to those skilled in the art. For example, a function approximating the spectral curve can be determined and maximum and minimum values can be calculated from the first and second derivatives of the function, using well known techniques.

As described in more detail in the examples, the analysis program can be designed to perform spectral subtractions in order to account for interferences between multiple components in a single gas. Alternatively, the subtraction can be performed chemically such as by selective scrubbing.

Because the "peak-to-trough" method of the present invention does not require an initial intensity value, $I_o$, it is well suited for use in in situ environments. This is because when one measures the concentrations of in situ gases, such as gases in a smoke stack, it is not possible to periodically purge the smoke stack in order to obtain a reference intensity value, $I_o$. Systems which use separate reference paths do not take into account the potential differences in radiation absorption that can be produced by the in-line optics. An additional advantage of devices which employ peak-to-trough analysis is that they require far fewer moving parts than a device employing $I_o$ measurements because operations such as purging, mechanical calibrations, alternate sample and reference paths, etc. can be eliminated.

EXAMPLES

EXAMPLE 1

Figure 3:
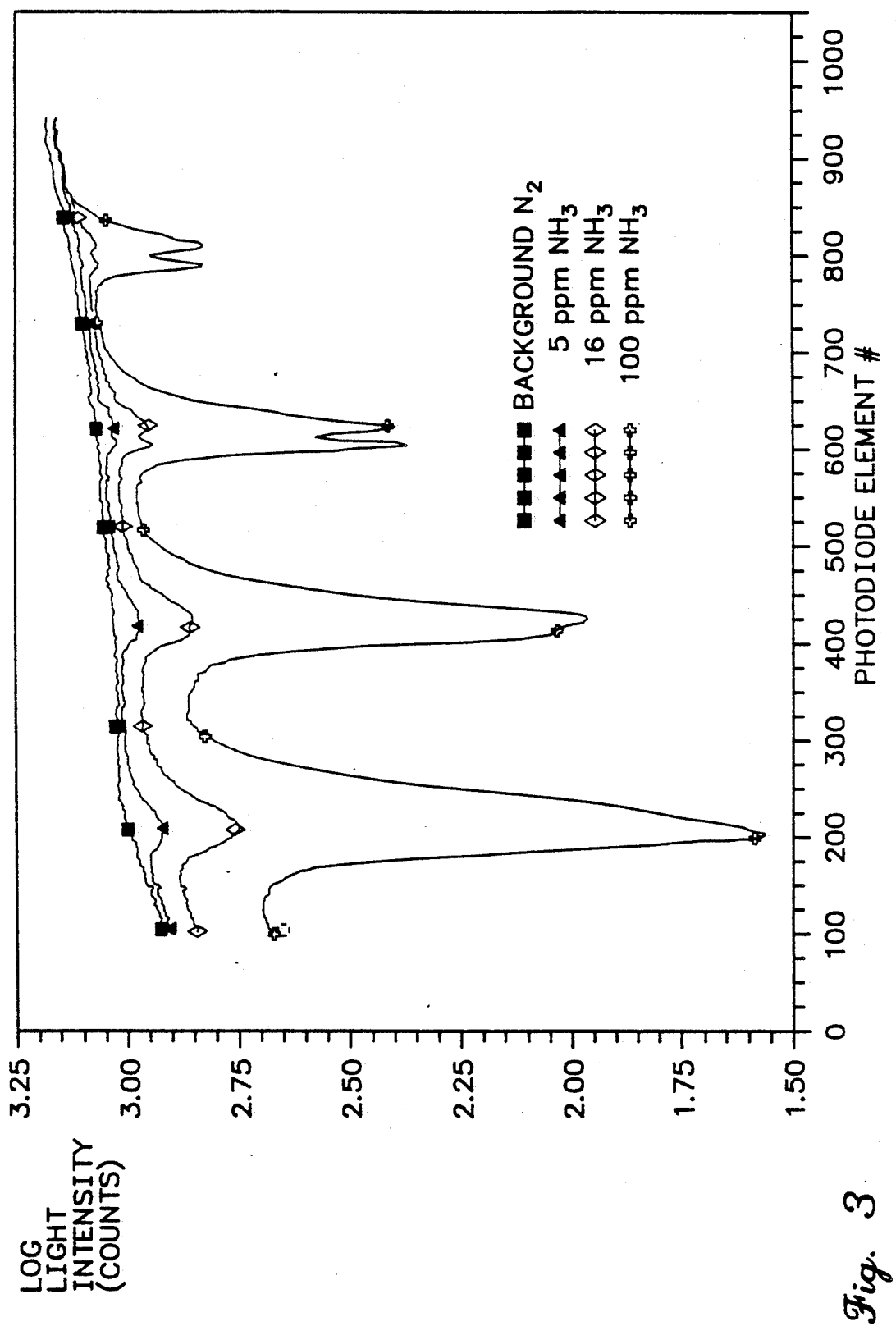
FIG. 3 illustrates spectra obtained for $NH_3$ at three different concentrations and for background $N_2$.

In order to demonstrate the present invention, the measurement of $NH_3$ in a flue gas will be described. To produce calibration curves, radiation intensity spectra were measured for various concentrations of $NH_3$ present in the gas cell. Radiation intensity spectra were measured for a range of $NH_3$ concentrations from 1 to 100 ppm. FIG. 3 shows characteristic spectra for three concentrations of $NH_3$. The spectra were plotted as log radiation intensity versus photodiode element number because the concentration is proportional to the log of the radiation intensity and the element numbers correspond to wavelengths. As can be seen from FIG. 3, as the concentration increases, the radiation intensity decreases in four distinct regions.

A nitrogen background spectrum was also plotted in FIG. 3. The upward slope of this spectrum is not due to absorbance by a gas but instead results from the transmittance characteristics of the optics. The wavelength increases from the lower photodiode element numbers to the higher numbers. Because the quartz optical elements are less efficient at transmitting shorter wavelength radiation, the intensity of transmitted radiation increases as the photodiode element numbers increase.

The radiation intensity spectra were analyzed using an algorithm for quantifying spectral data to produce an $NH_3$ calibration curve. The method capitalizes on Beer's law and eliminates the need to develop the absorbance spectra ($-\log I/I_o$). Quantitative data is taken directly as the difference between log values of the intensity spectrum of the sample gas at two distinct data points. This method speeds the computation time and eliminates the need for a zero gas or reference cell, thus simplifying the operation of the system. Therefore, the zero gas spectrum (background $N_2$) shown in FIG. 3 was not required for the analysis.

Two distinct data points used for the algorithm were chosen in a spectral region where a peak and trough occur. A search region is defined by diode numbers selected by the user and a computer routine searches for the minimum and maximum intensity values associated with the peak and trough, respectively. The height, or difference between the peak and trough, in log space is directly proportional to the concentration of the gas. The difference between the values for the minimum and maximum intensity values is used for establishing a calibration curve. The calibration curve can then be used with an inversion algorithm to determine the concentration of $NH_3$.

The diode search region used for quantifying the $NH_3$ spectra shown in FIG. 3 encompasses an absorbance peak located between diode 570 and diode 650. This absorbance peak with the first large doublet is centered near the 2080 Angstrom wavelength region. Quantitative analysis of $NH_3$ was based at this region because it presented a strong signal with minimal potential for interferences from other components found in flue gas.

Figure 4:
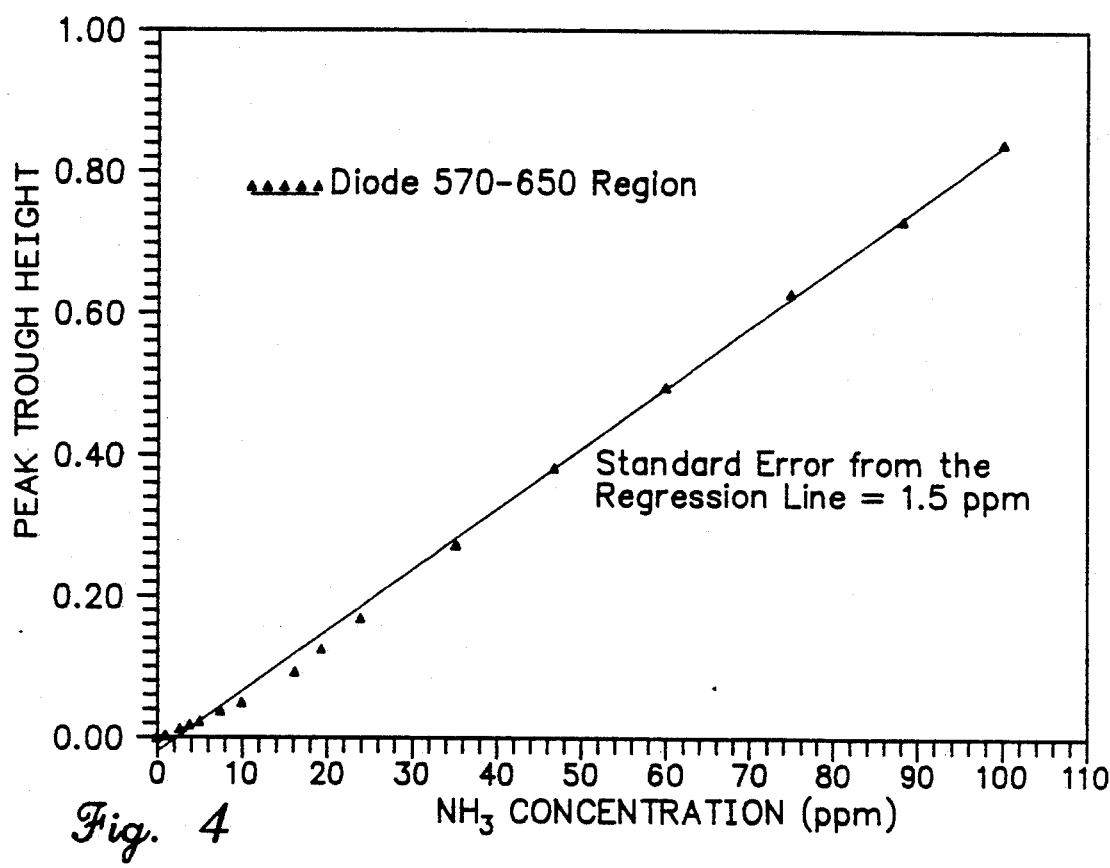
FIG. 4 illustrates an $NH_3$ calibration curve.

FIG. 4 shows the calibration curve for $NH_3$ concentrations between zero and 100 ppm established using the algorithm described above. A standard error of 1.5 ppm is the standard deviation of the data points from the first order curve fit of the data set. This data indicates that the instrument is capable of accurately measuring the concentration of $NH_3$ in the range of 0 to 100 ppm. This range and accuracy is suitable for most applications.

Figure 5:
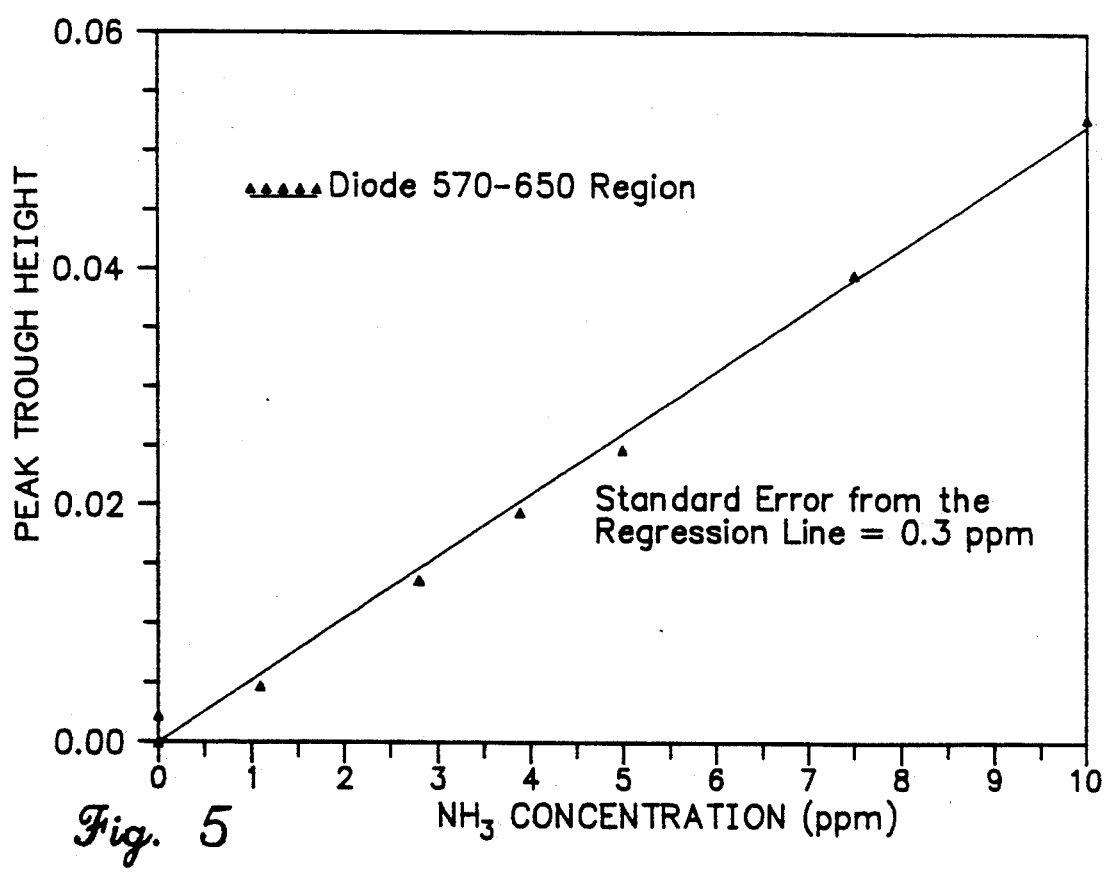
FIG. 5 illustrates another $NH_3$ calibration curve.

If increased precision is required for lower concentrations, then the instrument can be calibrated in the 1 to 10 ppm range as shown in FIG. 5. The standard deviation or error of the data points from the first order fit in this range is 0.3 ppm. This demonstrates that the instrument is capable of operating effectively for applications with stringent requirements for $NH_3$ concentration accuracy. This 0-10 ppm calibration is employed in the following examples to quantify $NH_3$ in the presence of interferences.

EXAMPLES 2-4

Several gases typically found in flue gas absorb radiation in the lower UV region and present a potential for interference with the measurement of $NH_3$. Therefore, experiments were conducted to measure intensity spectra for NO and $SO_2$ with a device according to the present invention. The results of this investigation into potential interferences are presented in Examples 2-4.

EXAMPLE 2

Figure 6:
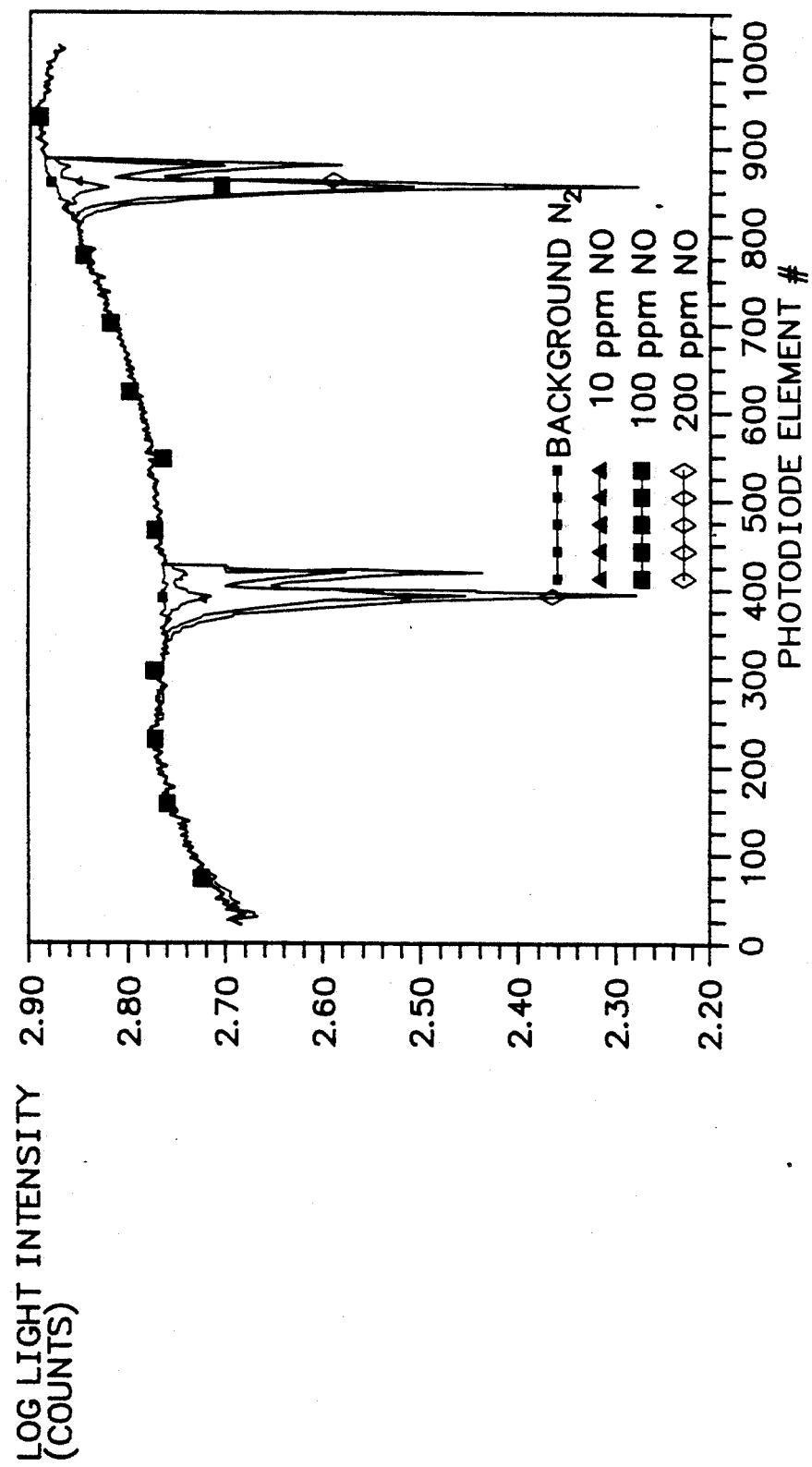
FIG. 6 illustrates spectra obtained for NO at three different concentrations and for background $N_2$.

Nitric oxide (NO) concentrations between 0 and 200 ppm were measured with the present device to determine its impact on the measurement of $NH_3$. FIG. 6 shows the spectra for three different concentrations of NO. In the wavelength region of interest, NO has two distinctive peaks with minimal radiation absorption between these peaks.

Figure 7:
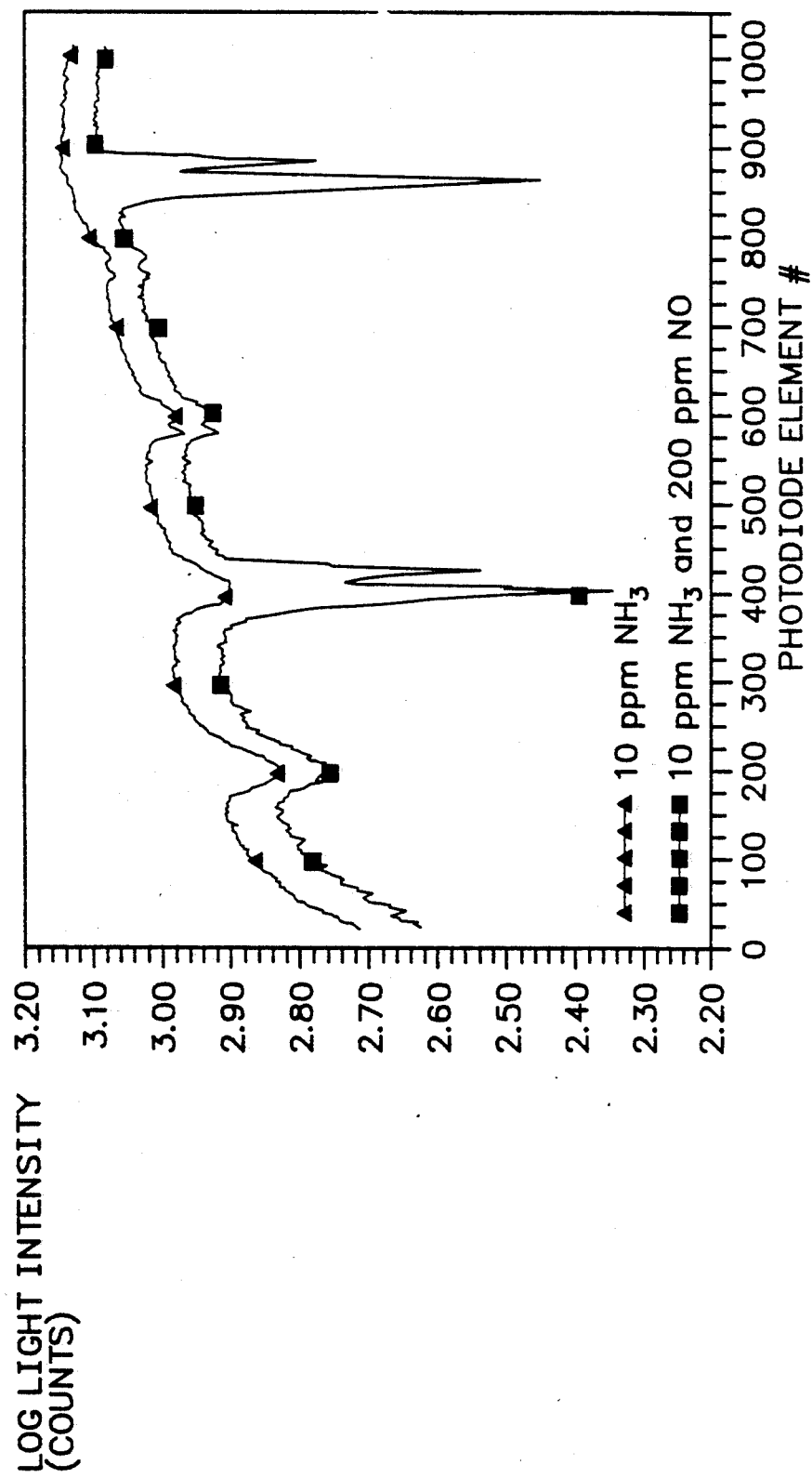
FIG. 7 illustrates spectra obtained for $NH_3$ alone and for a combination of $NH_3$ and NO.

FIG. 7 shows both a 10 ppm $NH_3$ spectrum and the spectrum produced by a gas mixture of 10 ppm $NH_3$ and 200 ppm NO. The peak and trough for the mixed gas sample occurring near diode 400 represents the radiation absorption of both $NH_3$ and NO and cannot be used for quantitative analysis of either gas without separating or compensating for the individual signals. However, both the $NH_3$ signal in the 570-650 diode region, i.e., 2070 Angstroms to 2090 Angstroms, and the NO signal in the 850-900 diode region, i.e., 2140 Angstroms to 2160 Angstroms, are unaffected by the presence of the other. Thus the present instrument can simultaneously measure both $NH_3$ and NO without any compensation or modification to the original signal.

It should be noted that in this example, a prism was employed as the polychromator. As a result, the resolution, i.e., the wavelength per diode, was not constant across the region of the spectrum of interest. As seen from the above figures, the resolution in the 570 to 650 diode region was approximately 0.25 Angstroms per diode, whereas in the 850 to 900 diode region the resolution was approximately 0.4 Angstroms per diode. In other examples a diffraction grating was used as a polychromator. When a diffraction grating is used, the resolution tends to be more constant across a given spectrum, as opposed to when a prism is employed and the resolution varies.

Figure 8:
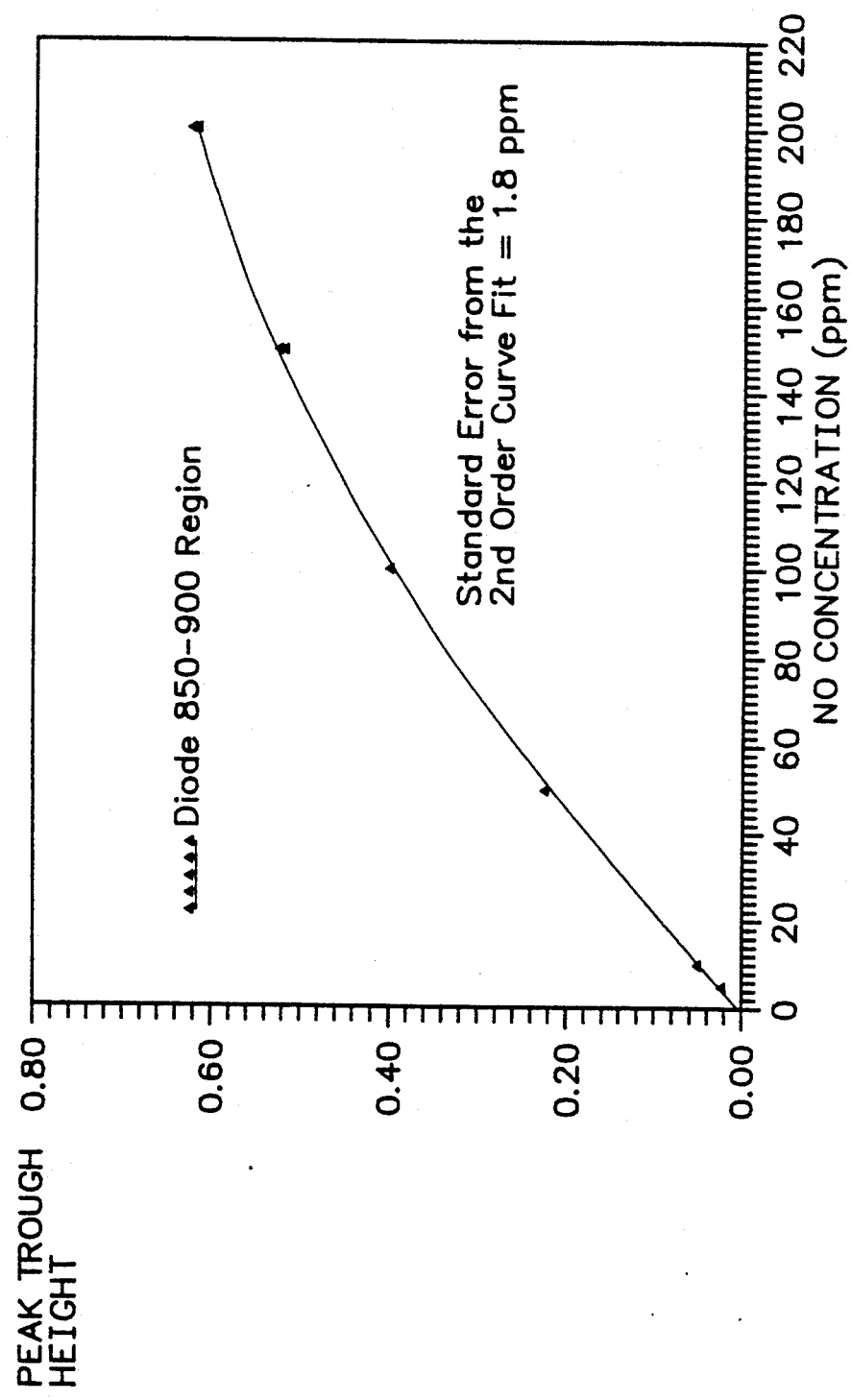
FIG. 8 illustrates an NO calibration curve.

A calibration curve for NO was established based on the peak-to-trough height measured in the 850–900 diode region and is shown in FIG. 8. A second order curve was fitted through the data and produced a standard error of 1.8 ppm over the range of 0–200 ppm NO.

The ability to measure $NH_3$ and NO was demonstrated by measuring intensity spectra of mixtures of the two gases. Concentrations of approximately 1 and 10 ppm of $NH_3$ were mixed with approximately 200 ppm of NO. The peak-to-trough algorithm was used with the calibration curves for $NH_3$ (FIG. 5) and NO (FIG. 8) to predict their concentrations. The results are presented in Table 1.

TABLE 1

MEASUREMENT OF $NH_3$ AND NO USING THE PHOTODIODE ARRAY SPECTROMETER

| ACTUAL $NH_3$ (ppm) | MEASURED $NH_3$ (ppm) | ACTUAL NO (ppm) | MEASURED NO (ppm) |
|---|---|---|---|
| 10 | 9.8 | 192 | 202 |
| 0.7 | 0.7 | 192 | 189 |

This data demonstrates that the instrument is capable of measuring 1 to 10 ppm levels of $NH_3$ in the presence of 1 to 200 ppm levels of NO. In fact, the instrument can accurately measure the concentrations of $NH_3$ and NO simultaneously. This is highly desirable because it is important to know the concentrations of both gases in order to optimize control processes for nitrogen oxides (collectively referred to as $NO_x$). The concentration ranges demonstrated in this example would fulfill the requirements of many potential applications.

EXAMPLE 3

Figure 9:
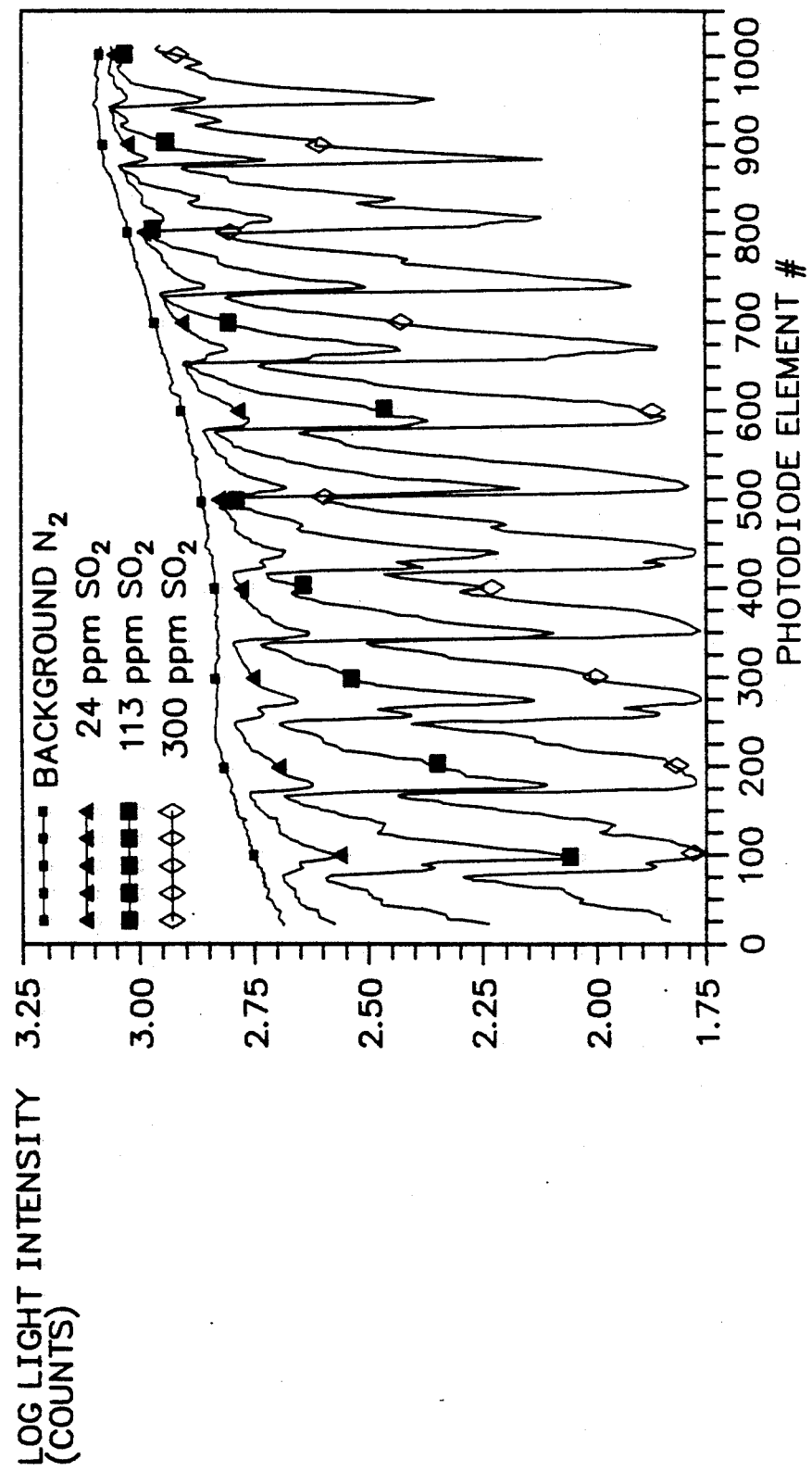
FIG. 9 illustrates spectra obtained for $SO_2$ at three different concentrations and for background $N_2$.

The interference of sulfur dioxide ($SO_2$) was investigated using the laboratory spectrometer. Spectra for several concentrations of $SO_2$ between 0–300 ppm were collected to determine the degree of interference to the measurement of $NH_3$. FIG. 9 shows three of these spectra. The $SO_2$ spectrum is a continuous series of bands through the 2090 Angstrom wavelength region with a radiation absorption strength slightly greater than that of an equivalent concentration of $NH_3$.

Figure 10:
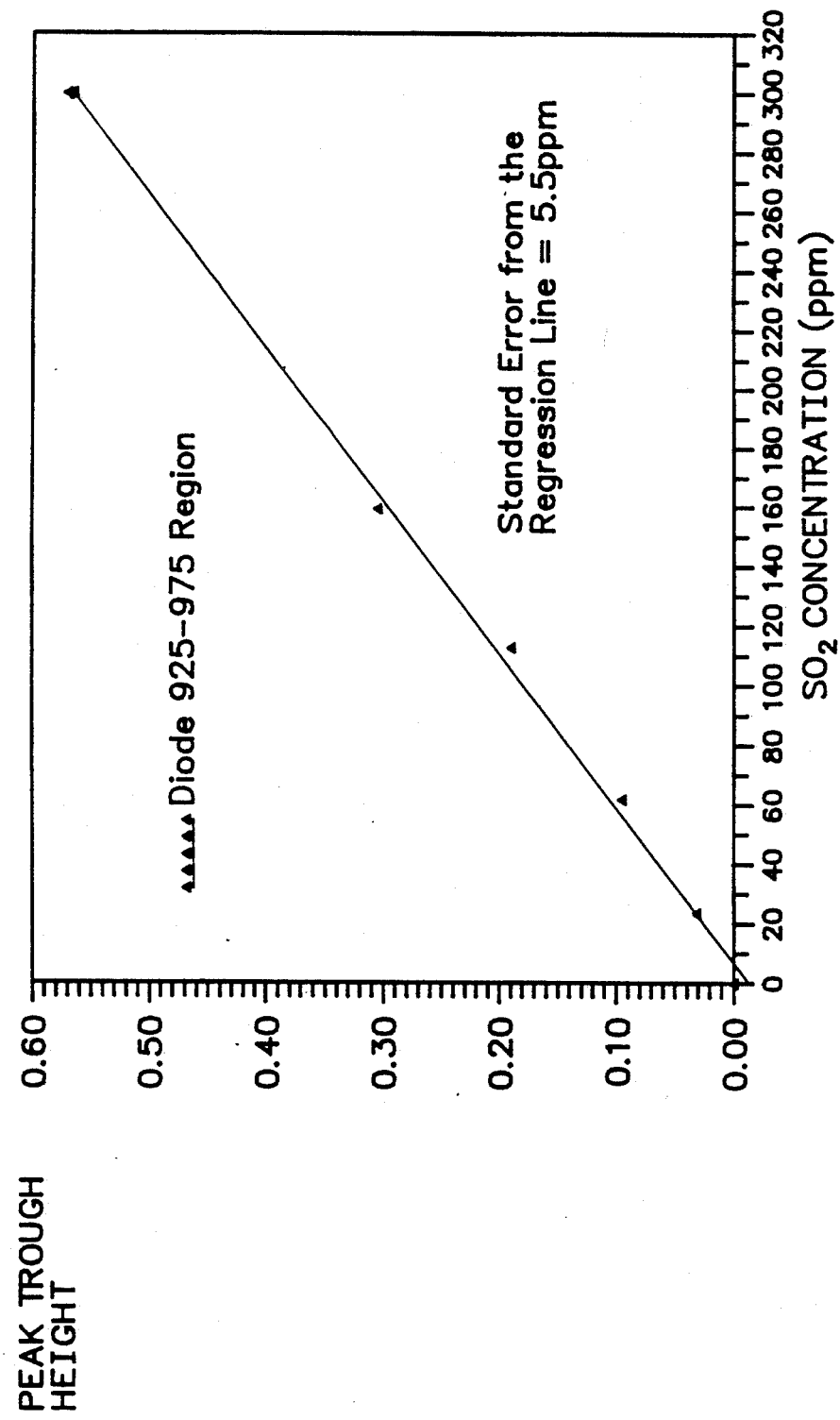
FIG. 10 illustrates a calibration curve for $SO_2$.

The peak-to-trough algorithm was used to analyze the $SO_2$ intensity spectra. Operating on the peak between diodes 925 and 975, i.e. 2170 Angstroms to 2200 Angstroms, the calibration curve shown in FIG. 10 was developed. The concentration of $SO_2$ in the range of 0 to 300 can be measured by the existing instrument with an accuracy of plus or minus 5.5 ppm.

To accurately measure $NH_3$ at low concentrations in flue gas streams containing $SO_2$, the signal produced by $SO_2$ can be eliminated by spectral subtraction prior to the $NH_3$ concentration calculation. Spectral subtraction involves the removal of an individual gas absorbance spectrum (e.g. $SO_2$) from a spectrum produced by a mixture of gases (e.g. $SO_2$ and $NH_3$). The photodiode array coupled with a computer make spectral subtraction of interferences a very effective technique.

Figure 11:
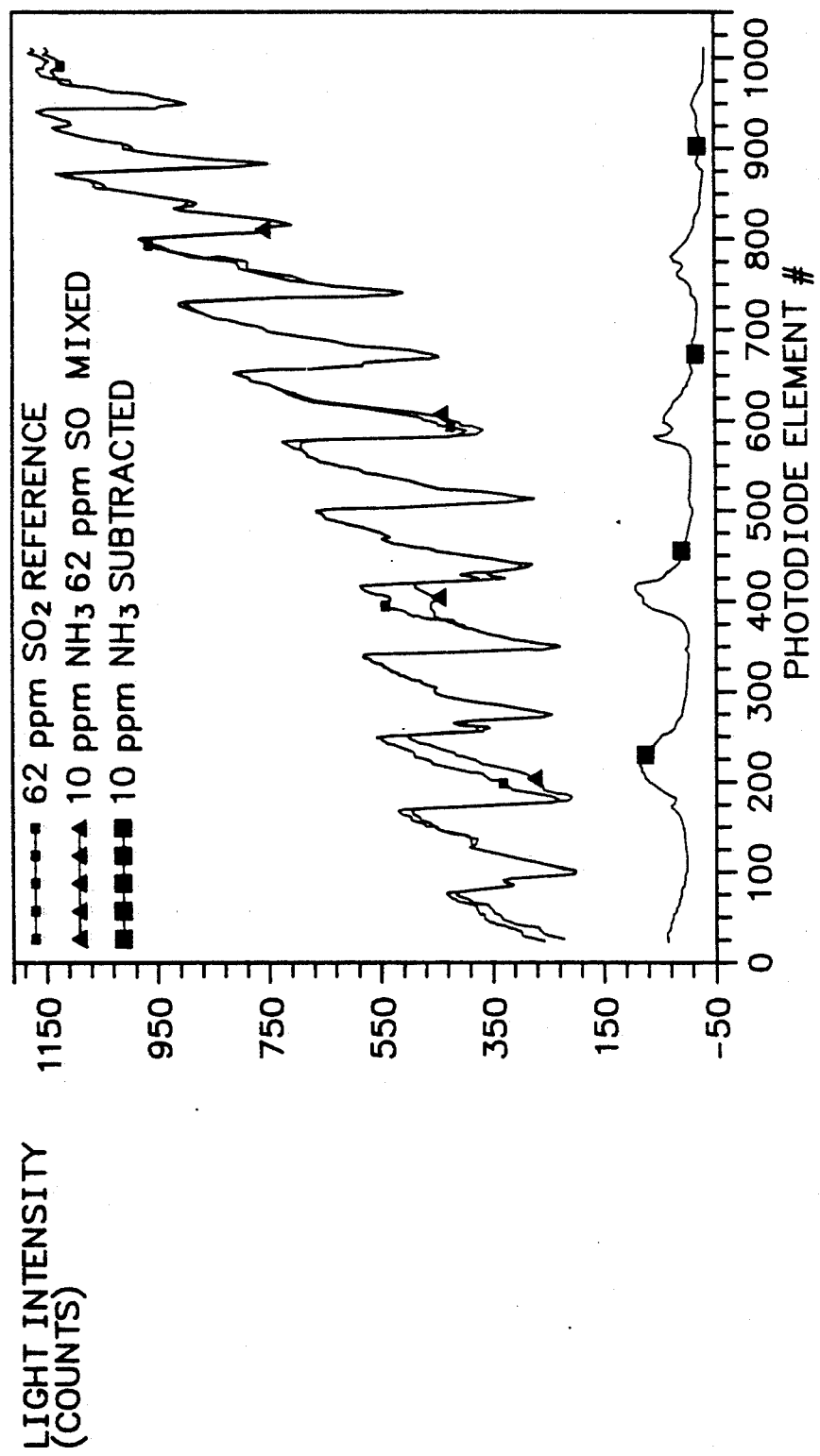
FIG. 11 illustrates a spectrum for $SO_2$ alone, a spectrum for a combination of $NH_3$ and $SO_2$ and an inverted spectrum for $NH_3$ after the $SO_2$ spectrum has been mathematically subtracted.

FIG. 11 is an example of the removal of $SO_2$ by spectral subtraction. In this example the spectrum of a gas mixture containing 10 ppm $NH_3$ and 62 ppm $SO_2$ is subtracted from a reference file of 62 ppm $SO_2$. The result is an inverted but very usable spectrum of $NH_3$. In practice the mixed gas spectrum is analyzed for the $SO_2$ concentration at a region where $NH_3$ does not absorb using the calibration curve shown in FIG. 10. A stored library reference file of spectra for various $SO_2$ concentrations is then modified to match the measured $SO_2$ concentration. This replicated $SO_2$ interference spectrum is then subtracted from the original mixed gas spectrum resulting in a spectrum due solely to $NH_3$ and other gases. The $NH_3$ concentration can then be quantified using the established calibration curves (See FIGS. 4, 5 and 13).

In order to experimentally validate the subtraction algorithm, experiments were conducted in which different concentrations of $NH_3$ were mixed with 300 ppm of $SO_2$. Intensity spectra were measured and subsequently analyzed using the spectral subtraction algorithm. The results ar presented in Table 2. As can been seen from the data, $NH_3$ concentrations in the range of 1 to 10 ppm can be measured in the presence of a 300 ppm background level of $SO_2$ with an accuracy of within about 1 ppm of $NH_3$.

TABLE 2

MEASUREMENT OF $NH_3$ WITH A 300 PPM $SO_2$ BACKGROUND USING SPECTRAL SUBTRACTION

| ACTUAL $NH_3$ CONCENTRATION (ppm) | MEASURED $NH_3$ CONCENTRATION (ppm) |
|---|---|
| 9.7 | 9.9 |
| 5.0 | 5.3 |
| 4.1 | 3.0 |

The spectral subtraction algorithm provides a means of eliminating the interference of low levels of $SO_2$ from the measurement of other gases, e.g. $NH_3$ and NO. Since this procedure already requires measuring of the concentration of $SO_2$, the present instrument can easily perform the simultaneous measurement of $NH_3$, NO, and $SO_2$.

It should be noted that in order for the spectral subtraction technique to perform adequately, the initial intensity of the radiation passing through the gases must remain constant, or vary in a known manner. If the initial radiation intensity, $I_o$, fluctuates in an unknown manner, error can be introduced when subtracting the $SO_2$ spectrum from the spectrum for the mixture of $SO_2$ and $NH_3$. The reason for this is that, although the concentration is calculated based on a peak-to-through height, the reference $SO_2$ spectra are only meaningful if the $I_o$ values are known. In other words, although changes in $I_o$ do not affect the concentration calculations performed in accordance with the present invention, the baseline of the spectra will vary if $I_o$ varies. Therefore, the difference between the intensity of the radiation entering the gas at the time the reference spectra are generated and the $I_o$ at the time the concentration measurements are made must be known in order for the spectral subtraction technique to result in accurate results. One general way in which to monitor the $I_o$ values is to check the radiation intensity in a wavelength region where no absorption occurs, if such a region exists. The amount of intensity variation can be correlated to the variation in $I_o$. If the variation in $I_o$ is unknown, it would be more appropriate to use a chemical subtraction technique, as described in Example 4, rather than the spectral subtraction technique.

EXAMPLE 4

The capable of laboratory instruments to measure low levels of $NH_3$ mixed with high concentrations of $SO_2$ is limited by the complete obscuring of all measurable radiation by $SO_2$ at concentrations above 500 ppm for the path length used in the present examples. Shortening the path length can raise the limiting $SO_2$ concentration but will also decrease the $NH_3$ measurement accuracy in the 0–10 ppm range. Therefore, an instrument can be designed to measure concentrations of $NH_3$ in the range of 5–100 ppm in the presence of high $SO_2$ levels for applications where the reduced accuracy at the lower level is acceptable.

For applications where spectral subtraction is inappropriate (e.g. when $I_o$ values are unknown or when high $SO_2$ concentrations are present and it is necessary to measure low level concentrations of $NH_3$), a non-mathematical means of eliminating the interference of $SO_2$ can be employed. Experiments were conducted to determine if it were possible to selectively eliminate $SO_2$ from the gas stream using a dry basic sorbent, e.g. calcium oxide, without reducing the concentration of $NH_3$.

The first set of tests was conducted to determine if low concentrations of $NH_3$ could pass through a scrubber containing calcium oxide sorbent without measurable losses. A mixture of gas containing 7.6 ppm of $NH_3$ was first measured directly by the spectrometer after by-passing the scrubber. A spectrum was then collected of the same gas after it passed through the scrubber to determine if there was a significant loss. The $NH_3$ concentration measured after the scrubber was 7.4 ppm. Since these two concentrations are within the accuracy of the instrument, it appears that there was minimal losses of $NH_3$ in the scrubber.

Next, a mixture comprising 2000 ppm $SO_2$ and 7.6 ppm $NH_3$ was passed through the packed-bed scrubber. The actual and measured $NH_3$ concentrations through the scrubber for both cases are summarized in Table 3. These tests demonstrate that it is possible to measure 1 to 10 ppm levels of $NH_3$ in a gas stream containing high concentrations of $SO_2$ using selective scrubbing.

TABLE 3

MEASUREMENT OF A LOW CONCENTRATION OF $NH_3$ IN A HIGH $SO_2$ BACKGROUND (2000 PPM) USING SELECTIVE SCRUBBING AND SPECTRAL SUBTRACTION

| ACTUAL $NH_3$ CONCENTRATION (PPM) | MEASURED $NH_3$ CONCENTRATION (PPM) | INLET $SO_2$ CONCENTRATION (PPM) |
| --- | --- | --- |
| 7.6 | 7.4 | 0 |
| 7.6 | 6.3 | 2000 |

An advantage of chemical removal of interfering gases (i.e., scrubbing) over mathematical removal (i.e., spectral subtraction) is that chemical removal is not affected by high $SO_2$ concentrations or by fluctuations in $I_o$.

EXAMPLE 5

Figure 12:
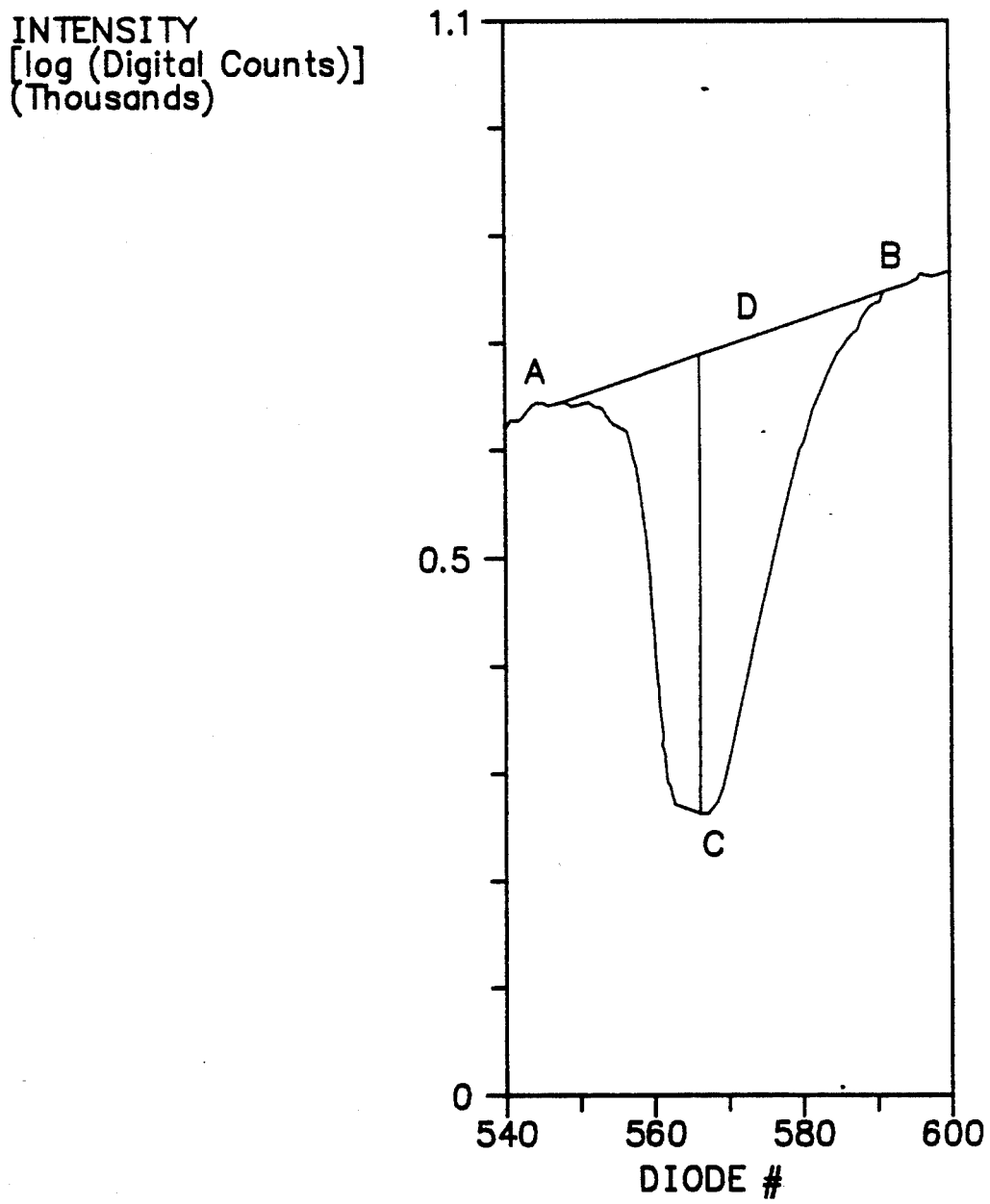
FIG. 12 illustrates a portion of a spectrum obtained for $NH_3$ used to illustrate the base line peak-to-trough method.

An experiment was conducted to determine the concentration of $NH_3$ using the peak-to-trough method and employing a calculated base line. The spectrum for $NH_3$ was obtained between diodes number 540 and 600, i.e. 2070 Angstroms to 2090 Angstroms, as shown in FIG. 12. Table 4 below lists the log intensity values corresponding to each diode number between 540 and 594.

TABLE 4

| Diode Number | Counts |
| --- | --- |
| 540 | 619 |
| 541 | 634 |
| 542 | 633 |
| 543 | 642 |
| 544 | 651 |
| 545 | 654 |
| 546 | 648 |
| 547 | 650 |
| 548 | 653 |
| 549 | 648 |
| 550 | 651 |
| 551 | 653 |
| 552 | 648 |
| 553 | 646 |
| 554 | 633 |
| 555 | 628 |
| 556 | 625 |
| 557 | 603 |
| 558 | 580 |
| 559 | 540 |
| 560 | 489 |
| 561 | 429 |
| 562 | 366 |
| 563 | 306 |
| 564 | 263 |
| 565 | 241 |
| 566 | 237 |
| 567 | 235 |
| 568 | 231 |
| 569 | 232 |
| 570 | 242 |
| 571 | 266 |
| 572 | 302 |
| 573 | 340 |
| 574 | 382 |
| 575 | 427 |
| 576 | 470 |
| 577 | 513 |
| 578 | 550 |
| 579 | 588 |
| 580 | 612 |
| 581 | 643 |
| 582 | 663 |
| 583 | 685 |
| 584 | 705 |
| 585 | 712 |
| 586 | 732 |
| 587 | 742 |
| 598 | 748 |
| 589 | 752 |
| 590 | 766 |
| 591 | 767 |
| 592 | 772 |
| 593 | 777 |
| 594 | 779 |

The minimum transmitted radiation level was determined. It corresponds to point C in FIG. 12 and to diode number 568 in Table 4. Two groups of data were selected at wavelengths above and below the wavelength corresponding to diode 568. The groups are chosen based on their location relative to the peak and lack of interference or noise. The first group starts 22 diode numbers below peak diode number 568 and the second group starts 22 diode numbers above peak diode number 568. These are indicated at A and B of FIG. 12. A linear regression operation was performed on the two groups, the first group being from diode numbers 546 to 550, and the second group being from diode numbers 590 to 594. The resultant line fit is line D illustrated in FIG. 12. The distance in log space is then calculated between point C and line D.

The calculations employed in Example 5 are summarized below.

Results obtained from linear regression calculation employing a standard least squares equation:

| Regression Output: | |
| --- | --- |
| Constant | −870.122 |
| Std Err of Y Est | 3.256403 |
| R Squared | 0.997736 |
| No. of Observations | 10 |
| Degrees of Freedom | 8 |
| X Coefficient(s) | 2.774074 |
| Std. Err of Coef. | 0.046711 |
| Measured Value at Diode 568 (Point C) | 231 |
| Log [Value at Diode 568] | 2.3636 |
| Calculated value at Diode 568 (On Line D) | 706 |
| Log [Calc. value at Diode 568] | 2.8488 |
| Log [Calc. Value] - LOG [Value] = | 0.4852 |

Figure 13:
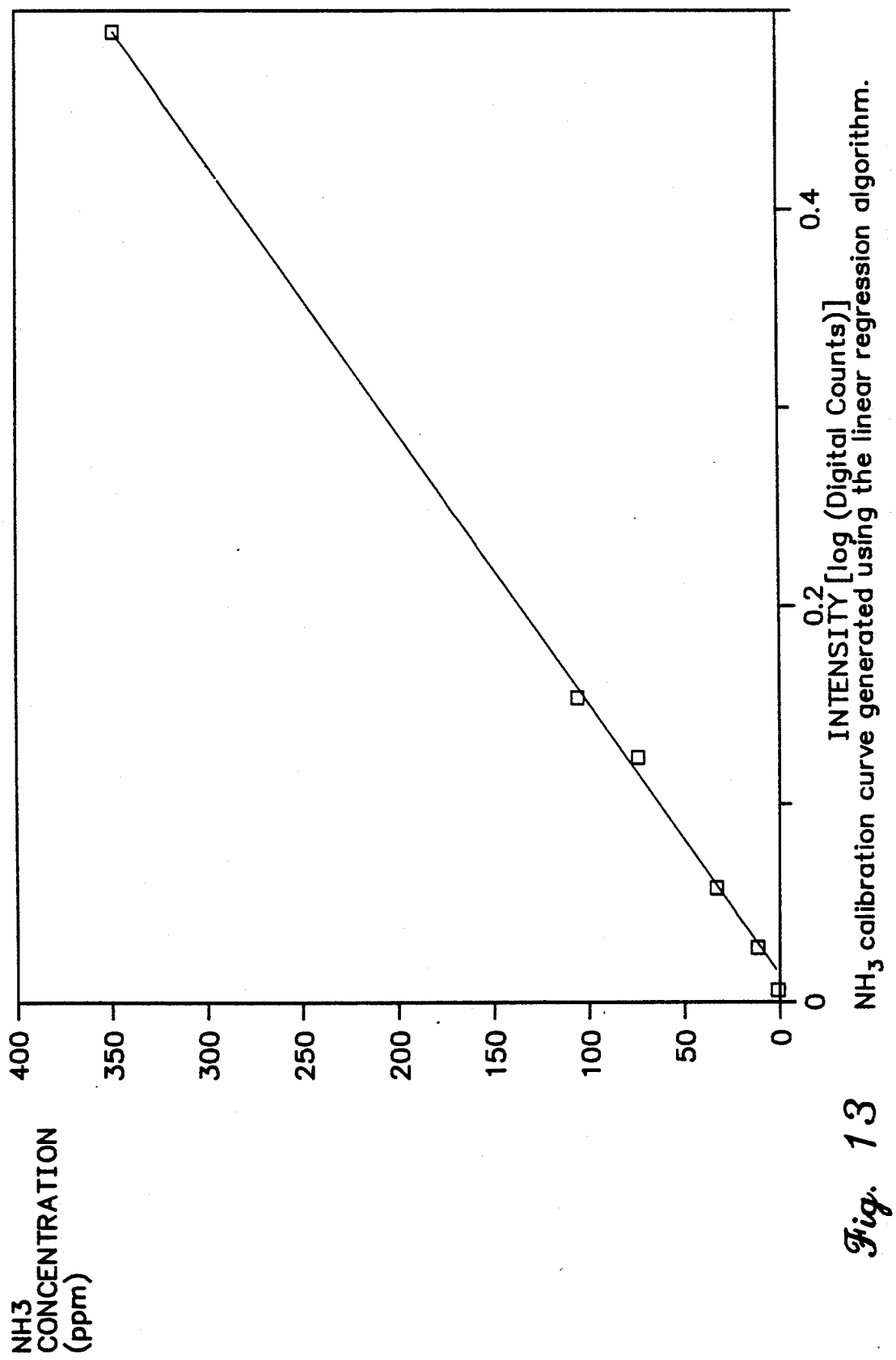
FIG. 13 illustrates a yet another $NH_3$ calibration curve.

The peak-to-trough height in log space, 0.4852, is then compared to the calibration line shown in FIG. 13 to determine the concentration of $NH_3$, in parts per million.

EXAMPLE 6

In order to evaluate the effects of resolution on the accuracy of concentration measurements, a comparison was made between an instrument having a resolution of one Angstrom per diode (high resolution) and an instrument having a resolution of 20 Angstroms per diode (low resolution). The resolution of the photodiode array depends upon the dispersion characteristics of the polychromater and the distance between the polychromater and the photodiode array, as well as the characteristics of the optics employed to collimate and focus the spectrum generated by the polychromater on the photodiode array. The instrument must be designed to provide sufficient resolution to differentiate the distinguishing features of the absorbance peaks of interest.

Figure 14:
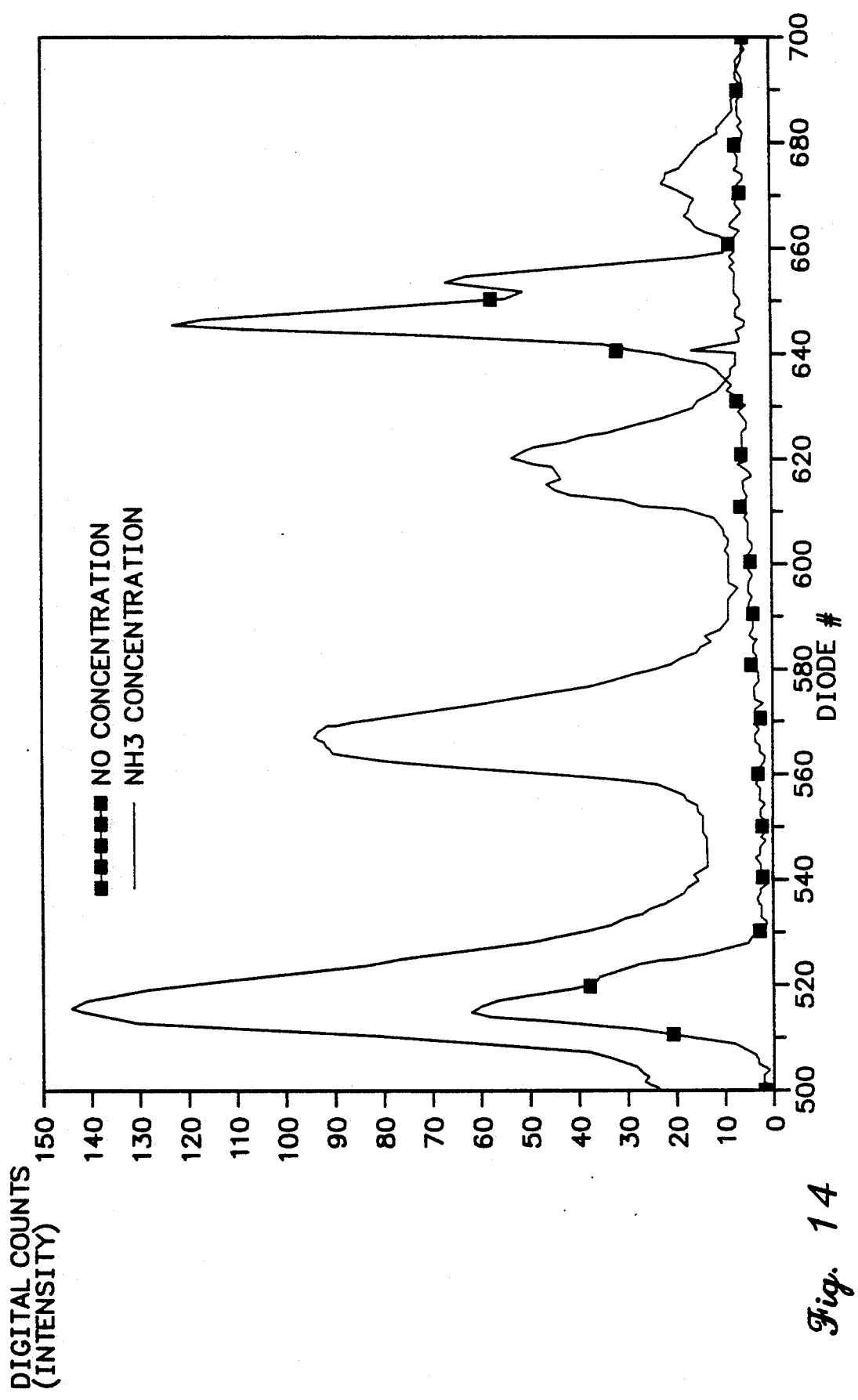
FIG. 14 illustrates spectra obtained using a device having a resolution of 1 Angstrom per diode.
Figure 15:
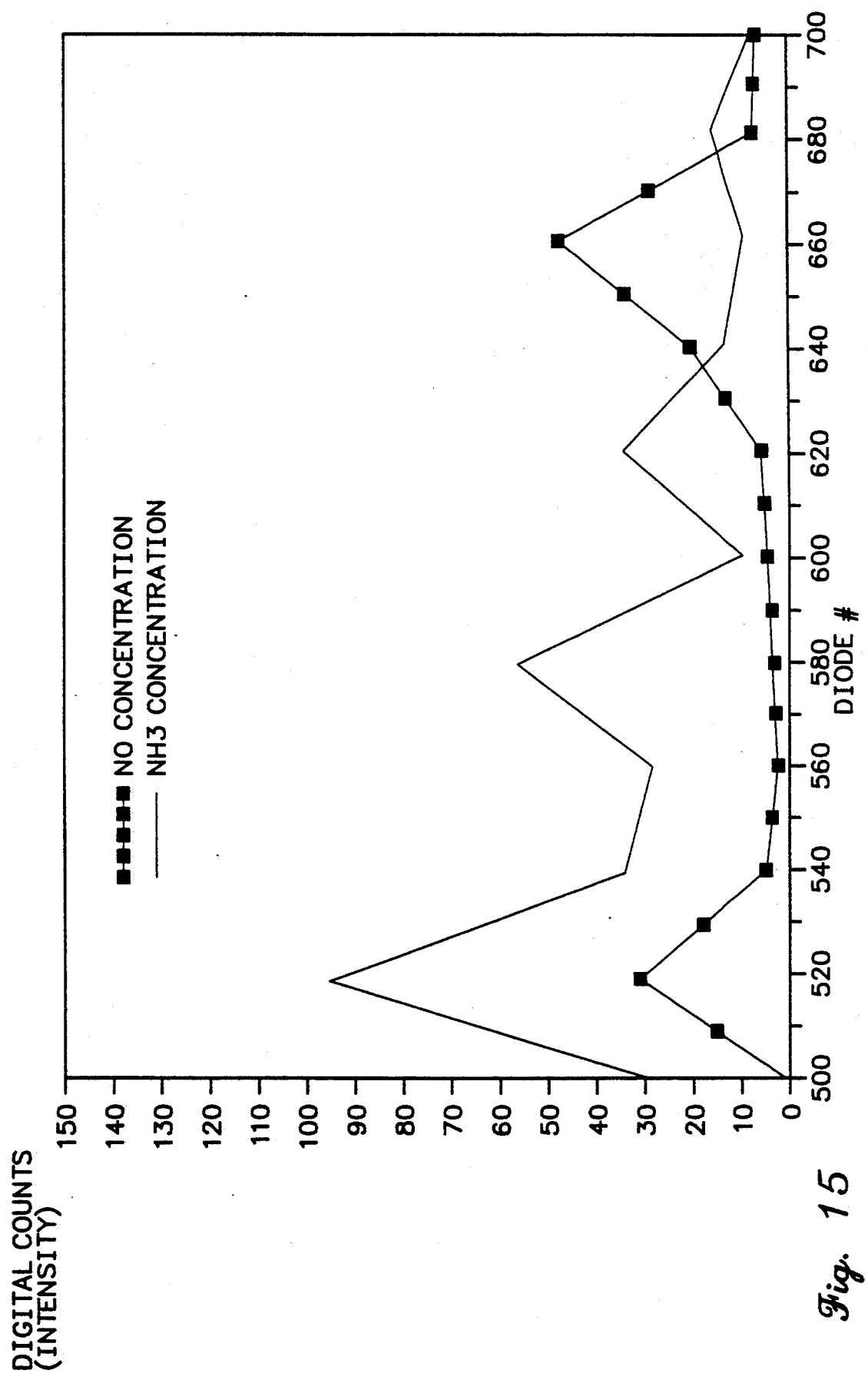
FIG. 15 illustrates the spectra of FIG. 14 with the resolution mathematically reduced to 20 Angstroms per diode.

FIG. 14 illustrates the absorbance spectra for equal concentrations of $NH_3$ and NO at a resolution of one Angstrom per diode. As can be seen, the NO peak between diodes 640 and 660 (centered on 2150 Angstroms) is separated and easily distinguished from the $NH_3$ peaks which occur adjacent to the NO peak on both sides. FIG. 15 shows the same absorbance spectra, except the resolution has been mathematically reduced to 20 Angstroms per diode. In addition to the loss in detail for the peaks, the adjacent peaks have begun to blend together. This produces an interference between the gases which would result in reduced accuracy. It should be noted that absorbance is inversely related to transmittance $(I/I_o)$. Therefore, the absorbance spectra appear inverted relative to the transmitted radiation spectra.

As will be appreciated by those skilled in the art, the present device and method can be employed to measure the concentrations of gases other than $NH_3$, NO and $SO_2$. In order to measure other gases, transmitted radiation spectra are first obtained at various known concentrations. Calibration curves are then calculated base on peak-to-trough heights within selected wavelength ranges. The selected wavelength ranges should correspond to absorbance peaks. Additionally, if the gases are to be measured in the presence of other gases, the absorbance peaks should be selected so that the gases are non-interfering. If this is not possible, as is the case with $SO_2$, mathematical spectral subtraction can be employed to measure gases in the presence of other interfering gases. Alternatively, chemical selective scrubbing can be employed. Examples of other gases which can be measured using the present device and method include aromatic hydrocarbons (e.g., benzene, toluene, xylene and phenol) formaldehyde, ozone, chlorine and bromine.

As will also be appreciated by those skilled in the art, the present device and method can be used on non-gaseous systems. For example, the present apparatus and method can be used to perform colorimetric analysis on liquids. Additionally, although the present invention has been described with specific examples employing absorbance in the ultraviolet region, absorbances in other wavelengths regions can be employed with equal results.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A method for in situ measurement of at least one component in a gas stream comprising:
    a) passing radiation through an in situ gas stream,
    b) selecting at least one wavelength range in which said component absorbs radiation,
    c) measuring the amount of radiation which passes through said gas stream at a plurality of wavelengths within said selected wavelengths range, and
    d) calculating the concentration of said component by comparing the difference in the amount of radiation which passes through said gas at two selected points within said selected wavelength range.

2. The method as claimed in claim 1 wherein said gas stream is a flue gas and the in situ environment is a smoke stack.

3. The method as claimed in claim 1 wherein said component is selected from the group consisting of NO, $SO_2$, $NH_3$, aromatic hydrocarbons, formaldehyde, ozone, chlorine and bromine.

4. The method as claimed in claim 1 wherein said step of calculating the concentration of the component comprises:
    a) determining a first wavelength at which minimum transmitted radiation occurs within said selected range,
    b) determining a second wavelength at which maximum transmitted radiation occurs within said selected range,
    c) determining the difference between said minimum transmitted radiation and said maximum transmitted radiation, and
    d) calculating the concentration of said component using reference data obtained from measurements performed on gases of known concentration.

5. The method as claimed in claim 1 wherein said step of calculating the concentration of a component comprises:

a) determining a first wavelength at which a minimal amount of radiation is transmitted within said selected range, b) calculating a base line by performing a linear regression calculation on two groups of transmitted radiation values within said selected range, the first group of transmitted radiation values corresponding to wavelengths less than said first wavelength and at which high transmission occurs and the second group of transmitted radiation values corresponding to wavelengths greater than said first wavelength and at which high transmission occurs, c) determining the difference between said minimal transmitted radiation value and said base line at said first wavelength, and d) calculating the concentration of said component using reference data obtained from measurements performed on gases of known concentration.

6. The method as claimed in claim 1 wherein at least two wavelengths ranges are selected in order to measure at least two components in said gas stream.

7. The method as claimed in claim 1 wherein the concentration of $NH_3$ in a gas stream is measured and the selected wavelength range is from about 2040 Angstroms to about 2120 Angstroms.

8. The method as claimed in claim 7 wherein the concentration of $NH_3$ is calculated by employing both the difference in the amount of radiation which passes through said gas at two selected points within said wavelength range and a calibration curve of the type illustrated in FIGS. 4, 5 and 13.

9. The method as claimed in claim 1 wherein the concentration of NO in a gas stream is measured and the selected wavelength range is from about 2100 Angstroms to about 2200 Angstroms.

10. The method as claimed in claim 9 wherein the concentration of NO is calculated by employing both the difference in the amount of radiation which passes through said gas at two selected points within said wavelength range and a calibration curve of the type illustrated in FIG. 8.

11. The method as claimed in claim 1 wherein the concentration of $SO_2$ in a gas stream is measured and the selected wavelength range is from about 2270 Angstroms to about 2300 Angstroms.

12. The method as claimed in claim 11 wherein the concentration of $SO_2$ is calculated by employing both the difference in the amount of radiation which passes through said gas at two selected points within said wavelength range and a calibration curve of the type illustrated in FIG. 10.

13. A device for in situ measurement of components in a gas stream comprising:

a) a radiation source;

b) a radiation detection means for measuring radiation transmitted through said gas stream at a plurality of wavelengths within at least one selected wavelength range, c) means for passing radiation from said radiation source through said in situ gas stream before impinging on said radiation detection means, wherein said means comprises components which are positionally fixed during the measuring of said radiation, d) calculation means for determining the concentration of a component in said gas stream by employing the transmitted radiation values obtained for said selected wavelength range to obtain a deference between a maximum transmitted radiation value and a minimum transmitted radiation value within said selected wavelength range and comparing said difference to calibration values obtained by measuring relative transmitted radiation values for gases of known concentration within said selected wavelength range.

14. The device as claimed in claim 13 wherein said components include $NH_3$, NO and $SO_2$ which are individually or simultaneously present in said gas stream.

15. The device as claimed in claim 13 wherein said radiation detection means comprises a linear photodiode array having a resolution from about 1 to about 4 Angstroms per diode.

16. The device as claimed in claim 13 wherein said radiation detection means comprises a linear photodiode array having a resolution of about one Angstrom per diode.

17. A method for calculating the concentration of a component in a fluid comprising:

a) selecting a wavelength range, wherein said component absorbs radiation at some wavelengths within said wavelength range, b) passing radiation through said fluid, c) measuring the amount of radiation transmitted at wavelengths within said wavelength range, d) determining a first wavelength at which the minimum amount of radiation is transmitted within said wavelength range, e) calculating a base line for said wavelength range, said base line passing through points of relatively high transmitted of radiation values, f) calculating the difference between said base line and said minimum transmitted radiation point at said first wavelength, and g) calculating the concentration of the component based on said difference.

18. The method as claimed in claim 17 wherein the concentration of $NH_3$ is a gas stream is calculated and the selected wavelength range is from about 2040 Angstroms to about 2120 Angstroms.

19. The method as claimed in claim 18 wherein the concentration of $NH_3$ is calculated by employing both the log values of said difference and a calibration curve of the type illustrated in FIGS. 4, 5 and 13.

20. The method as claimed in claim 17 wherein said component is $NH_3$ and said base line is calculated by performing a linear regression operation on a first group of selected points corresponding to transmitted radiation values for wavelengths in the range of from about 20 to about 50 Angstroms less than said first wavelength and a second group of selected points corresponding to transmitted radiation values for wavelengths in the range of from about 20 to about 50 Angstroms more than said first wavelength.

21. The method as claimed in claim 17 wherein the concentration of NO in a gas stream is calculated and the selected wavelength range is from about 2200 Angstroms to about 2300 Angstroms.

22. The method as claimed in claim 21 wherein the concentration of NO is calculated by employing both the log values of said difference and a calibration curve of the type illustrated in FIG. 8.

23. The method as claimed in claim 17 wherein said component is NO and said base line is calculated by performing a linear regression operation on a first group of selected points corresponding to transmitted radiation values for wavelengths in the range of from about 20 to about 50 Angstroms less than said wavelength and a second group of selected points corresponding to transmitted radiation values for wavelengths in the range of from about 20 to about 50 Angstroms more than said first wavelength.

24. The method as claimed in claim 17 wherein the concentration of $SO_2$ gas in a gas stream is calculated and the selected wavelength range is from about 2170 Angstroms to about 2200 Angstroms.

25. The method as claimed in claim 24 wherein the concentration of $SO_2$ is calculated by employing both the log values of said difference and a calibration curve of the type illustrated in FIG. 10.

26. The method as claimed in claim 17 wherein said component is $SO_2$ and said base line is calculated by performing a linear regression operation on a first group of selected points corresponding to transmitted radiation values for wavelengths in the range of from about 15 to about 25 Angstroms less than said first wavelength and a second group of selected points corresponding to transmitted radiation values for wavelengths in the range of from about 15 to about 25 Angstroms more than said first wavelength.

27. A device for determining the concentrations of at least one component in a fluid comprising:
 a) a positionally fixed radiation source;
 b) a positionally fixed chromator,
 c) a positionally fixed filter,
 d) a positionally fixed radiation detection means capable of sensing the intensity of incident radiation within at least one selected wavelength range, and
 e) means to convert the output from the radiation detection means to a concentration for the desired component based upon a single reading of radiation intensities across said selected wavelength range and using a predetermined calibration curve.

28. A device as claimed in claim 27 wherein said fluid is a gas and said component is $NH_3$.

29. A device as claimed in claim 27 wherein said fluid is a gas and said component is NO.

30. A device as claimed in claim 27 wherein said fluid is a gas and said component is $SO_2$.

31. A device as claimed in claim 27 wherein said radiation source comprises a deuterium lamp which produces ultraviolet and visible radiation in the wavelength region of from about 1900 to about 6000 Angstroms.

32. A device as claimed in claim 27 wherein said polychromator comprises a prism or an optical grating.

33. A device as claimed in claim 27 wherein said filter comprises a slit.

34. A device as claimed in claim 27 wherein said radiation detection means comprises a linear photodiode array.

35. A device as claimed in claim 27 wherein said radiation detection means comprises a linear photodiode array having a resolution effective for identifying appropriate peaks and preventing the undesirable blending of adjacent peaks.

36. A device as claimed in claim 27 wherein said radiation detection means comprises a linear photodiode array having a resolution from about 1 to about 4 Angstroms per diode.

37. A device as claimed in claim 27 wherein said radiation detection means comprises a linear photodiode array having a resolution of about one Angstrom per diode.

38. A method for measuring the concentration of a component in a sample comprising:
 a) passing radiation through said sample,
 b) dispersing said radiation in order to generate a spectrum,
 c) measuring the intensity of a selected wavelength range within said spectrum after said radiation has passed through said sample,
 d) determining the difference between the maximum transmitted radiation and the minimum transmitted radiation within said selected range,
 e) calculating the concentration of said component by comparing said difference to previously determined differences for known concentrations.

39. The method as claimed in claim 38 wherein said step of measuring the intensity of a selected wavelength range within said spectrum is accomplished using a radiation detection means comprising a linear photodiode array having a resolution of from 1 to about 4 Angstroms per diode.

40. The method as claimed in claim 38 wherein said step of measuring the intensity of a selected wavelength range within said spectrum is accomplished using a radiation detector comprising a linear photodiode array having a resolution of approximately one Angstrom per diode.

41. A method for determining the concentration of $NH_3$, NO and $SO_2$ in a gas stream comprising:
 a) measuring the intensity of radiation passing through the gas stream at wavelengths which correspond to absorption by $SO_2$ between about 2170 Angstroms and about 2200 Angstroms,
 b) employing peak-to-trough calculations to determine the concentration of $SO_2$,
 c) determining the spectrum corresponding to the $SO_2$ alone based upon the peak-to-trough calculations and predetermined calibration curves,
 d) mathematically subtracting the spectrum due to $SO_2$ alone from the overall spectrum,
 e) measuring the intensity of radiation passing through the gas stream at wavelengths which correspond to absorption by $NH_3$ between about 2040 Angstroms and about 2120 Angstroms,
 f) employing peak-to-trough calculations to determine the concentration of $NH_3$,
 g) measuring the intensity of radiation passing through the gas stream at wavelength which corresponds to absorption by NO between about 2200 Angstroms and about 2300 Angstroms,
 i) employing peak-to-trough calculations to determine the concentration of NO.

42. The method as claimed in claim 41 further comprising the step of chemically removing $SO_2$ from the gas stream by selective scrubbing prior to the calculation of $NH_3$ and NO concentration.

* * * * *

UNITED STATES PATENT AND TRADEMARK OFFICE
CERTIFICATE OF CORRECTION

PATENT NO. : 5,070,246

DATED : December 3, 1991

INVENTOR(S) : Durham et al.

Page 1 of 2

It is certified that error appears in the above-identified patent and that said Letters Patent is hereby corrected as shown below:

Column 2, line 6 after "mixture" insert a period.

Column 6, line 8 after "20" insert a period.

Column 6, line 10 after "pathlength" insert a period.

Column 6, line 17 after "process" insert a period.

Column 6, line 27 after "conditions" insert a period.

Column 6, line 34 after "present" insert a period.

Column 12, line 24 delete "ar" and substitute --are-- therefor.

Column 15, line 66 delete "base" and substitute --based-- therefor.

Column 16, line 21 delete "wavelengths" and substitute --wavelength-- therefor.

Column 16, line 38 delete "wavelengths" and substitute --wavelength-- therefor.

Column 16, line 41 delete "comparing" and substitute --determining-- therefor.

UNITED STATES PATENT AND TRADEMARK OFFICE
CERTIFICATE OF CORRECTION

PATENT NO. : 5,070,246
DATED : December 3, 1991
INVENTOR(S) : Durham et al.

It is certified that error appears in the above-identified patent and that said Letters Patent is hereby corrected as shown below:

Column 17, line 68 delete "deference" and substitute --difference-- therefor.

Signed and Sealed this

Twenty-fifth Day of May, 1993

Attest:

MICHAEL K. KIRK

*Attesting Officer*   *Acting Commissioner of Patents and Trademarks*